United States Patent
Hla et al.

(10) Patent No.: US 10,870,689 B2
(45) Date of Patent: Dec. 22, 2020

(54) APOM-FC FUSION PROTEINS, COMPLEXES THEREOF WITH SPHINGOSINE 1-PHOSPHATE (S1P), AND METHODS FOR TREATING VASCULAR AND NON-VASCULAR DISEASES

(71) Applicant: Children's Medical Center Corporation, Boston, MA (US)

(72) Inventors: Timothy T. Hla, Wellesley, MA (US); Steven L. Swendeman, Cambridge, MA (US); Annarita DiLorenzo, Ithaca, NY (US); Teresa Sanchez, Ithaca, NY (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/326,089

(22) PCT Filed: Aug. 15, 2017

(86) PCT No.: PCT/US2017/046916
§ 371 (c)(1),
(2) Date: Feb. 15, 2019

(87) PCT Pub. No.: WO2018/052615
PCT Pub. Date: Mar. 22, 2018

(65) Prior Publication Data
US 2019/0185545 A1 Jun. 20, 2019

Related U.S. Application Data

(60) Provisional application No. 62/375,088, filed on Aug. 15, 2016.

(51) Int. Cl.
| | | |
|---|---|---|
| C07K 14/775 | (2006.01) | |
| C07K 19/00 | (2006.01) | |
| A61K 38/17 | (2006.01) | |
| A61K 8/55 | (2006.01) | |
| A61P 9/10 | (2006.01) | |
| A61P 9/02 | (2006.01) | |
| C07K 14/00 | (2006.01) | |
| A61K 9/00 | (2006.01) | |
| A61K 47/54 | (2017.01) | |
| A61P 9/12 | (2006.01) | |
| A61K 38/00 | (2006.01) | |

(52) U.S. Cl.
CPC .......... *C07K 14/775* (2013.01); *A61K 8/553* (2013.01); *A61K 9/0019* (2013.01); *A61K 38/1709* (2013.01); *A61K 47/544* (2017.08); *A61P 9/02* (2018.01); *A61P 9/10* (2018.01); *A61P 9/12* (2018.01); *C07K 14/00* (2013.01); *C07K 19/00* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 2011/0178029 A1* | 7/2011 | Knudsen | C07K 14/775 514/21.2 |
| 2013/0195849 A1 | 8/2013 | Spreter Von et al. | |
| 2013/0324701 A1 | 12/2013 | Williams et al. | |
| 2014/0303086 A1 | 10/2014 | Hla et al. | |
| 2016/0184458 A1 | 6/2016 | Heartlein | |
| 2017/0360749 A1 | 12/2017 | Harijith et al. | |

FOREIGN PATENT DOCUMENTS

| | | | | |
|---|---|---|---|---|
| WO | WO-2006000448 A2 * | 1/2006 | | C07K 16/46 |
| WO | WO 2010/049103 A1 | 5/2010 | | |
| WO | WO 2017/031353 A1 | 2/2017 | | |
| WO | WO 2018/052615 A1 | 3/2018 | | |
| WO | WO 2019/035931 A1 | 2/2019 | | |

OTHER PUBLICATIONS

Christoffersen et al., Endothelium-protective sphingosine-1-phosphate provided by HDL-associated apolipoprotein M. Proc Natl Acad Sci U S A. Jun. 7, 2011;108(23):9613-8.
Wang et al., Immunoglobulin Fc domain fusion to TRAIL significantly prolongs its plasma half-life and enhances its antitumor activity. Mol Cancer Ther. Mar. 2014;13(3):643-50.
Yu et al., Immunoglobulin Fc domain fusion to apolipoprotein (a) kringle V significantly prolongs plasma half-life without affecting its anti-angiogenic activity. Protein Eng Des Sel. Jun. 2013;26(6):425-32.
Zauner et al., Glycoproteomic analysis of antibodies. Mol Cell Proteomics. Apr. 2013;12 (4):856-65.
U.S. Appl. No. 16/639,445, filed Feb. 14, 2020, Hla et al.
PCT/US2018/000202, Feb. 27, 2020, International Preliminary Report on Patentability.
PCT/US2019/055831, Jan. 7, 2020, International Search Report and Written Opinion.
EP 17581271.1, Dec. 18, 2019, Extended European Search Report.
EP 17581271.1, Jan. 10, 2020, Extended European Search Report.
Burg et al., Sphingosine 1-Phosphate Receptor 1 Signaling Maintains Endothelial Cell Barrier Function and Protects Against Immune Complex-Induced Vascular Injury. Arthritis Rheumatol. Nov. 2018;70(11):1879-1889.

(Continued)

*Primary Examiner* — Zachary C Howard
(74) *Attorney, Agent, or Firm* — Wolf, Greenfield & Sacks, P.C.

(57) ABSTRACT

The present disclosure is directed to an engineered phospholipid or lysophospholipid (e.g., sphingosine 1-phosphate (S1P)) chaperone derived from an Apolipoprotein M (ApoM)-Fc fusion protein having an extended half life in vivo. The disclosed ApoM-Fc fusion protein provides a safe, efficient and effective means of delivering S1P to endothelial cells and to all tissues of the body.

17 Claims, 11 Drawing Sheets
Specification includes a Sequence Listing.

(56) References Cited

OTHER PUBLICATIONS

Kaplan et al., TRAIL (Apo2 ligand) and TWEAK (Apo3 ligand) mediate CD4+ T cell killing of antigen-presenting macrophages. J Immunol. Mar. 15, 2000;164(6):2897-904.

Snoek et al., Sphingolipids in Congenital Diaphragmatic Hernia; Results from an International Multicenter Study. PLoS One. May 9, 2016;11(5).

Swendemen et al., An engineered S1P chaperone attenuates hypertension and ischemic injury. Sci Signal. Aug. 15, 2017;10(492).

Wu et al., Pharmacokinetics of Peptide-Fc fusion proteins. J Pharm Sci. Jan. 2014;103(1):53-64. doi: 10.1002/jps.23783. Epub Nov. 27, 2013.

PCT/US2018/000202, Nov. 30, 2018, International Search Report and Written Opinion.

PCT/US2017/46916, Jan. 2, 2018, International Search Report and Written Opinion.

\* cited by examiner

US 10,870,689 B2

APOM-FC FUSION PROTEINS, COMPLEXES THEREOF WITH SPHINGOSINE 1-PHOSPHATE (S1P), AND METHODS FOR TREATING VASCULAR AND NON-VASCULAR DISEASES

CROSS REFERENCE TO RELATED APPLICATIONS

This application is a national stage filing under 35 U.S.C. § 371 of international application number PCT/US2017/046916, filed Aug. 15, 2017, which claims the benefit of priority from U.S. Provisional Application No. 62/375,088, filed Aug. 15, 2016, the entire contents of each of which are incorporated herein by reference.

STATEMENT REGARDING FEDERALLY SPONSORED RESEARCH OR DEVELOPMENT

This invention was made with government support under Grant No. HL089934 awarded by the National Institutes of Health. The government has certain rights in the invention.

INCORPORATION BY REFERENCE OF SEQUENCE LISTING

The Sequence Listing in an ASCII text file, named as 33974_Seq_ST25.txt of 6 KB, created on Aug. 9, 2017, and submitted to the United States Patent and Trademark Office via EFS-Web, is incorporated herein by reference.

BACKGROUND

Endothelial cell function is essential for normal cardiovascular homeostasis (Harrison, D. G., *Basic research in Cardiology*, 89 Suppl 1, 87-102 (1994); Pober, J. S. & Sessa, W. C., *Nature Reviews. Immunology*, 7, 803-815 (2007)). Many environmental and intrinsic risk factors for cardiovascular and cerebrovascular diseases cause endothelial dysfunction. Indeed, dysfunctional endothelium is thought to initiate the development of vascular diseases (Girouard, H. & Iadecola, C., *J. of App. Physiology*, 100, 328-335 (2006)). On the other hand, various endogenous factors promote the well-being of the endothelium and counteract the risk factors (Libby, P. et al., *J. of the Am. Coll. of Cardio.* 54, 2129-2138 (2009)). One such factor is high-density lipoprotein (HDL), a multifunctional circulating nanoparticle (Rosenson, R. S. et al., *Nature Rev. Cardiology*, 13, 48-60 (2016)).

Numerous epidemiological studies have shown that plasma HDL levels are correlated with reduced risk from cardiovascular and cerebrovascular diseases (Hovingh, G. K. et al., *Curr. Op. in Lipidology*, 26, 127-132 (2015); Rader, D. J., *Nature Med.*, 18, 1344-1346 (2012)) as well as improved outcomes after an ischemic event (Makihara, N. et al., *Cerebrovascular Diseases*, 33, 240-247 (2012); Olsson, A. G. et al., *European Heart Journal*, 26, 890-896 (2005)). However, pharmacologic elevation of total HDL-cholesterol by cholesterol ester transfer protein inhibitors or niacin supplementation did not reduce cardiovascular outcomes (Keene, D. et al., *BMJ*, 349, g4379 (2014)). In addition, HDL particles are heterogeneous, contain numerous bioactive factors and regulate vascular, metabolic and immune functions (Rye, K. A., *Journal of Lipid Research*, 50 Suppl, S195-200 (2009)), suggesting that specific HDL particle subtypes regulate unique functions in the cardiovascular system. For example, it was recently demonstrated that plasma apolipoprotein M-containing HDL (ApoM$^+$HDL) is a physiological carrier of the bioactive lipid sphingosine 1-phosphate (S1P) that acts on G protein-coupled S1P receptors, suppress inflammatory responses and maintain vascular barrier function (Christensen, P. M. et al., *FASEB J.*, 30.6 (2016): 2351-2359 (2016); Christoffersen, C. et al., *PNAS*, 108, 9613-9618 (2011); Galvani, S. et al., *Science Signaling*, 8, ra79 (2015)). Regarding S1P-dependent immune actions, ApoM$^+$HDL is not required for lymphocyte egress from secondary lymphoid organs, but rather restrains lymphopoiesis in the bone marrow (Blaho, V. A. et al., *Nature*, 523, 342-346 (2015)). Mice that lack ApoM have alterations in lipoprotein metabolism and exhibit enhanced atherosclerosis in the LDL receptor null background. In addition, adenoviral expression of ApoM suppresses atherosclerosis in LDL receptor null mice (Wolfrum, C. et al., *Nature Med.*, 11, 418-422 (2005); Christoffersen, C. et al., *J. of Biol. Chem.*, 283, 1839-1847 (2008)). Plasma ApoM is positively correlated with HDL, LDL and cholesterol while negatively correlated with acute—myocardial infarction, endotoxemia, diabetes, metabolic syndrome and BMI (Frej, C. et al., *JCMM*, 20.6 (2016): 1170-1181 (2016); Borup, A. et al., *Current Opinion in Lipidology*, 26, 48-55 (2015); Nielsen, L. B. et al., *Trends in Endocrinology and Metabolism*, 20, 66-71 (2009), Plomgaard, P. et al., *Journal of Internal Medicine*, 266, 258-267 (2009)). Together, these observations suggest that ApoM$^+$HDL promotes endothelial function and that this signaling pathway is compromised in cardiovascular, inflammatory and metabolic diseases.

Sphingosine-1-phosphate (S1P), the phosphorylated metabolite of D-sphingosine, binds to five G protein-coupled receptors (S1P1-S1P5) and regulates a plethora of biological actions (Garcia et al., *J. Clin. Invest*, 108:689-701 (2001); Ishii et al., *Annu. Rev. Biochem.*, 73:321-354 (2004)). In particular, the prototypical S1P1 receptor is essential for vascular maturation during development and promotes endothelial cell migration, angiogenesis and barrier functions (Liu et al., *J. Clin. Invest*, 106:951-961 (2000); Paik et al., *J. Biol Chem.*, 276:11830-11837 (2001); Lee et al., *Cell*, 99:301-312 (1999)). Thus, S1P is required for maintenance of the barrier property of the lung endothelium (Camerer et al., *J. Clin. Invest*, 119:1871-1879 (2009)). Plasma S1P, which is derived from several cellular sources (Pappu et al., *Science*, 316:295-298 (2007); Venkataraman et al., *Circ. Res.*, 102:669-676 (2008)), is associated with high density lipoprotein (HDL) (~65%) and albumin (~35%) (Aoki et al., *J. Biochem.*, 138:47-55 (2005); Argraves et al., *J. Lipid Res.*, 48:2325-2333 (2007)). HDL-induced vasorelaxation as well as barrier-promoting and pro-survival actions on the endothelium have been attributed to S1P signalling (Kimura et al., *J. Biol Chem.*, 281:37457-37467 (2006); Nofer et al., *J. Clin. Invest*, 113:569-581 (2004); Argraves et al., *J. Biol Chem.*, 283:25074-25081 (2008)). Hence, much of the endothelium-protective actions of HDL are due to the actions of S1P on the endothelial S1P receptors.

The S1P chaperone Apolipoprotein M (ApoM) is a ~22-kDa HDL-associated apolipoprotein and a member of the lipocalin family of proteins which mainly resides in the plasma HDL fraction (X U et al., *J. Biol Chem.*, 274:31286-31290 (1999)). Mature ApoM (Human apoM, SEQ ID NO: 9 (GenBank Accession No: NP_061974.2), and murine ApoM, SEQ ID NO: 10 (GenBank Accession No: NP_061286.1)) retains the signal peptide (amino acids 1-21 of SEQ ID No: 9 and SEQ ID NO:10), which serves as a lipid anchor attaching ApoM to the phospholipid layer of the lipoproteins, thereby keeping it in the circulation and preventing filtration of ApoM in the kidney (Christoffersen et al., *J. Biol Chem.*, 283:18765-18772 (2008)).

ApoM contains a lipid-binding pocket that associates with S1P and a tethered signal peptide that allows it to anchor to the HDL particle (Axler, O. et al., *FEBS Letters* 582, 826-828 (2008)). S1P binding affinity to its receptors is higher than to ApoM, which presumably allows S1P release from the chaperone followed by receptor association and activation (Christoffersen, C. et al., *PNAS*, 108, 9613-9618 (2011); Sevvana, M. et al., *Journal of Molecular Biology*, 404, 363-371 (2010); Lee, M. J. et al., *Science*, 279, 1552-1555 (1998)). Recent studies show that HDL-bound S1P acts as a "biased agonist" on endothelial S1P1 receptor, which means that only a subset of downstream responses are activated (Galvani, S. et al., *Science Signaling*, 8, ra79 (2015)). HDL-bound S1P is important for endothelial survival, migration, angiogenesis, NO production and inhibition of inflammatory responses (Galvani, S. et al., *Science Signaling*, 8, ra79 (2015); Nofer, J. R. et al., *JCI*, 113, 569-581 (2004); Nofer, J. R. et al., *JBC*, 276, 34480-34485 (2001); Kimura, T. et al., *JBC*, 281, 37457-37467 (2006)). In addition, HDL-bound S1P likely engages both HDL receptors (SR-B1, etc.) as well as S1P receptors to evoke specific biological responses such as stimulation of NO synthesis, inhibition of endothelial injury and inflammation (Sato, K., *World Journal of Biological Chemistry*, 1, 327-337 (2010)).

SUMMARY OF THE DISCLOSURE

In one aspect, this disclosure provides a fusion protein comprising an Apolipoprotein M (ApoM) polypeptide fused to a fragment crystallizable (Fc) region of an antibody.

In some embodiments, the ApoM polypeptide comprises amino acids 21-188 of SEQ ID NO: 9. In some embodiments, the ApoM polypeptide comprises the amino acid sequence as set forth in SEQ ID NO: 9.

In some embodiments, the Fc region is fused to the amino terminus of the ApoM polypeptide. In some embodiments, the Fc region is fused to the carboxyl terminus of the ApoM polypeptide.

In some embodiments, the Fc region is an Fc region selected from the group consisting of an IgG antibody, an IgM antibody, an IgA antibody, an IgE antibody, and an IgD antibody. In a specific embodiment, the Fc region is an IgG1-Fc.

In another aspect, this disclosure provides a composition comprising an ApoM fusion protein in complex with phospholipids or lysophospholipids.

In some embodiments, the phospholipids comprise phosphocholine. In some embodiments, the phospholipids comprise sphingosine 1-phosphate (S1P).

In some embodiments, the composition is formed by mixing the fusion protein with the phospholipids or lysophospholipids, incubating the mixture to allow the complex to form, and purifying the complex.

In still another aspect, the disclosure provides a method of treating a condition in a subject, comprising administering a composition comprising an ApoM-Fc fusion protein in complex with phospholipids or lysophospholipids to the subject, wherein said condition is selected from the group consisting of hypertension, ischemia of the heart, ischemia of the brain, accelerated atherosclerosis, non-cardiac reperfusion injury and peripheral vascular disease.

In some embodiments, said hypertension comprises conditions selected from the group consisting of primary resistant hypertension, secondary resistant hypertension, neurogenic hypertension, gestational hypertension (pre-eclempsia), diabetic pre-eclempsia, and hypertension of chronic kidney disease.

In some embodiments, said ischemia of the heart comprises diseases selected from the group consisting of cardiac reperfusion injury, myocardial infarction, acute coronary syndrome and angina.

In some embodiments, said non-cardiac reperfusion injury comprises an injury as a result of an ischemia selected from the group consisting of liver ischemia, kidney ischemia, intestinal ischemia, and muscle ischemia.

In a further aspect, the disclosure provides a method of reducing a side effect of Fingolimod in a patient being treated with Fingolimod, comprising administering an ApoM-Fc fusion protein to the patient.

μM), or both and analyzed by immunoblot analysis for activation of p44/42 ERK and Akt. N=2-3; a representative blot is shown.

Figures 3A, 3B, 3C:
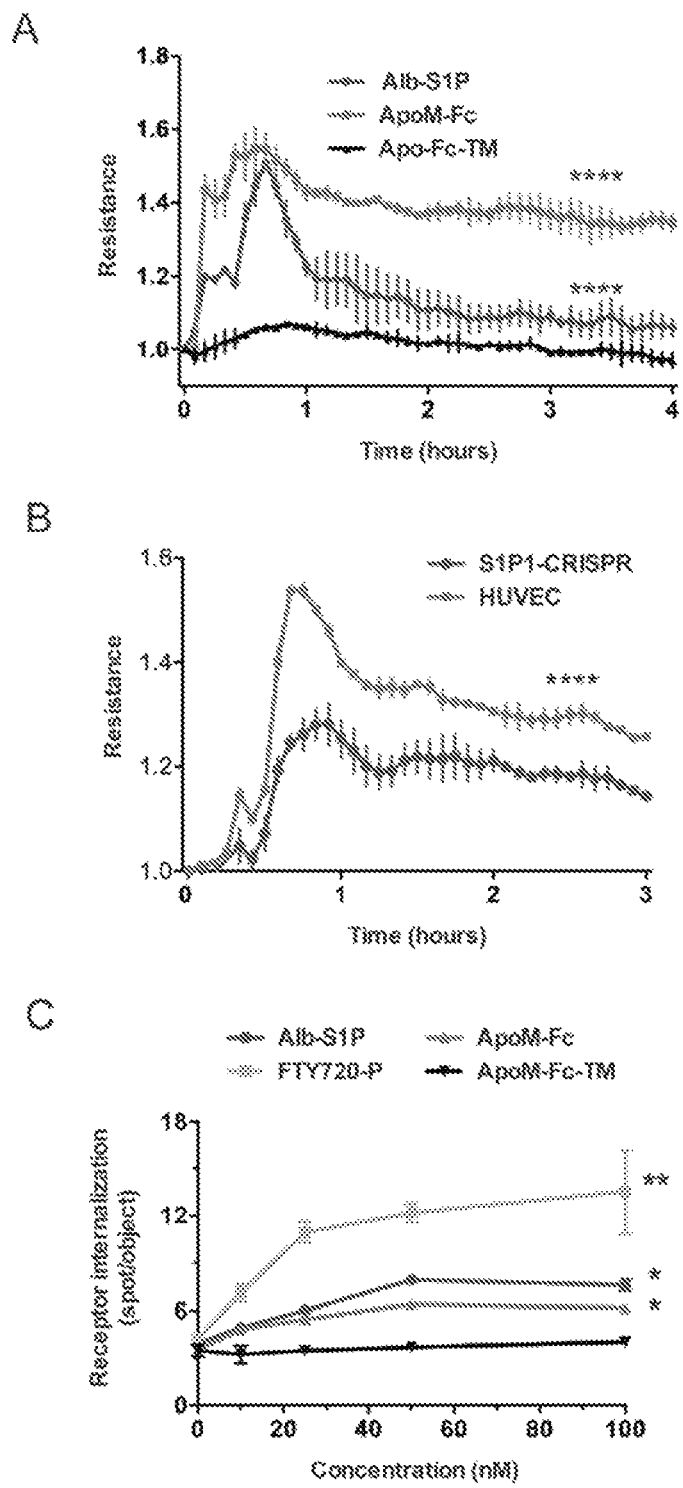

FIG. 3A-3C. Effect of ApoM-$F_c$ on S1P receptor endocytosis and endothelial cell barrier function. (A) HUVEC were analyzed for barrier function by real-time measurement of TEER as described. At time 0, either Alb-S1P (200 nM) or ApoM-Fc (20 μg/ml; 200 nM) or ApoM-$F_c$-TM (20 μg/ml) was added. All data were compared to baseline ApoM-$F_c$-TM (N=3; expressed as Mean (+S.E.M) t-test, **, P<0.0001; two-way ANOVA, P<0.0001). (B) HUVEC or S1P$_1$ KO HUVEC (S1P$_1$-CRISPR) were treated with ApoM-$F_c$ (10 μg/ml; 100 nM) and analyzed for barrier function by real-time measurement of TEER as described. (t-test, , P<0.0001; one-way ANOVA, P<0.0001). (C) U2OS cells expressing S1P$_1$-GFP were treated with indicated concentrations of FTY720-P, BSA-S1P, ApoM-$F_c$ or ApoM-$F_c$-TM for 30 min at 37° C., fixed and receptor internalization was quantified as described. All data were compared to baseline ApoM-$F_c$-TM (N=2, n=8; expressed as Mean (+s.e.m) t-test , P<0.01; *, P<0.05, One-way ANOVA, P<0.01).

Figures 4A, 4B, 4C:
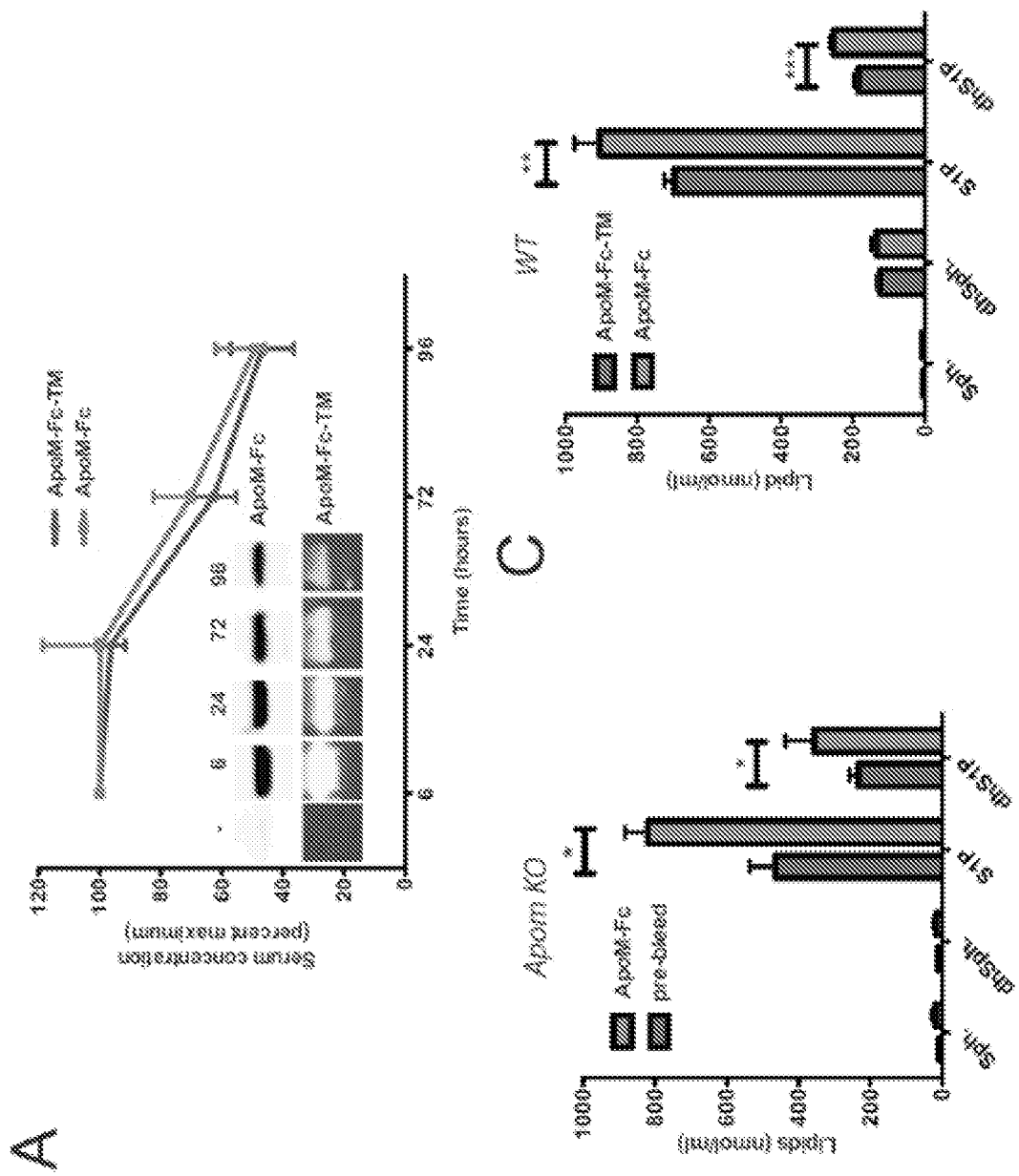

FIG. 4A. Effect of ApoM-Fc administration on plasma S1P levels and circulating hematopoietic cells. (A) WT mice were treated with 4 mg/kg of purified ApoM-$F_c$ or ApoM-$F_c$-TM (N=4) by intraperitoneal injection and plasma ApoM level was determined by immunoblot analysis as described. (B) Apom$^{-/-}$ mice (N=4, expressed as Mean (+S.D.)) were administered ApoM-$F_c$-S1P (4 mg/kg) and plasma sphingolipids at 24 h post-administration were quantified as described. (C) WT mice (N=4, expressed as Mean (+S.D.)) were administered 4 mg/kg of purified ApoM-Fc-S1P or ApoM-Fc-TM by intraperitoneal injection and plasma sphingolipids at 24 h post-administration were quantified as described. For B and C data were analyzed by two-tailed StudentÕs t-test (*p=0.05; p<0.01**p<0.005). (D)-(G) WT mice were administered either PBS (N=5), 4 mg/kg of purified ApoM-Fc-S1P (N=5) or ApoM-$F_c$-TM (N=5) by intraperitoneal injection and blood was collected at 6 and 24 hours post injection. Blood cells were isolated by centrifugation and Lymphocytes (D), White Blood Cells (WBC) (E), Red Blood Cells (RBC) (F) and platelets (G) were quantified by clinical grade cytometry. The observed variations in relative blood cells counts were statistically insignificant as judged by two-way ANOVA.

FIG. 5A-5E. ApoM-$F_c$ administration leads to sustained antihypertensive effect in mice. (A) Systolic blood pressure (SBP) was measured indicated times in AngII-treated mice administered with either vehicle (PBS) (N=2) or 4 mg/kg of ApoM-$F_c$ (N=6) or ApoM-$F_c$-TM (N=4) by intraperitoneal injection. (B) AngII-treated mice were injected with the S1P1 antagonist W146 (10 mg/kg) every 24 h (arrows) for followed by measurement of SBP. (N=5,5) (C) ApoM-$F_c$ or ApoM-$F_c$-TM was administered to AngII-treated mice (N=6) for 24 h and plasma nitrite levels were measured as described. (D) SBP was measured in normotensive mice administered with vehicle (PBS) (N=2) or 4 mg/kg of either ApoM-$F_c$ (N=6) or ApoM-$F_c$-TM (N=4) by intraperitoneal injection. (E) SBP was measured in WT (N=12) or Apom$^{-/-}$ (N=11) mice as described. All data are expressed as the mean±Standard Error of Mean (S.E.M.); *P<0.05; P<0.01; *P<0.001 compared to wild type (WT) (A-D). Statistical significance was determined by two-way ANOVA followed by Bonferroni's post hoc test or one-way ANOVA.

FIG. 6A-6H. ApoM-$F_c$ administration attenuates ischemia/reperfusion injury in heart and the brain. WT mice were administered PBS or 4 mg/kg of either ApoM-Fc (N=9) or ApoM-Fc-TM (N=9) by intravenous injection, 30 minutes prior to Myocardial Ischemia/Reperfusion surgery. Animals were subjected to 30 minutes of ischemia, followed by 24 hours of reperfusion. (A) Quantitative measurement of area at risk (AAR)/left ventricle (LV) area and infarct/AAR area was performed on the following cohorts in a blinded manner-PBS (N=7), ApoM-$F_c$-TM (N=9) and ApoM-$F_c$ (N=9). (B) Heart sections were stained with Ly6G and IB4 antibodies, and neutrophils and capillary density were quantified. N=9. (C) LV end-diastolic diameter (LVDd), LV end systolic (LVDs) diameter, and fractional shortening (FS) were measured at the indicated time points after myocardial I/R injury (n=6). Data are expressed as mean±SEM. *P<0.05, P<0.01, *P<0.001 compared with ApoM-$F_c$ group. (D) Mice were subjected to 60 minutes of focal cerebral ischemia by Middle cerebral artery occlusion (MCAO). Right after reperfusion, mice received 4 mg/kg of either ApoM-Fc (N=10), ApoM-$F_c$-TM (N=10), or PBS (N=10), by intraperitoneal injection. Infarct and (E) edema ratios were calculated by image analysis and reported as a ratio of the non-ischemic hemisphere. Infarct ratios were corrected for edema. (F) Total infarct volume in mm$^3$, corrected for edema. (G) Neurological deficit scores were assessed 23 hours after reperfusion. (H) Relative cerebral blood flow (rCBF) in the middle cerebral artery (MCA) territory was measured by laser speckle during MCAO surgery. The relative CBF (% of contralateral, CL) during occlusion (designated as "I") and after reperfusion (designated as "R") are shown. The individual values and the mean±S.E.M. are shown. *P<0.05 (one-way non-parametric ANOVA followed by Dunn's test).

DETAILED DESCRIPTION

Definitions

As used herein, the term "about" refers to an approximately ±10% variation from a given value.

The term "acute coronary syndrome" (ACS) refers to a syndrome due to decreased blood flow in the coronary arteries such that part of the heart muscle is unable to function properly or dies. The most common symptom of ACS is chest pain, often radiating to the left shoulder or angle of the jaw, associated with nausea and sweating. Acute coronary syndrome is usually caused by one of three problems: ST elevation myocardial infarction (STEMI, 30% of the cases), non ST elevation myocardial infarction (NSTEMI, 25% of the cases), or unstable angina (38% of the cases).

The term "angina" refers to chest pain or discomfort that occurs when an area of the heart muscle does not get enough oxygen.

The term "atherosclerosis" refers to the pathologic processes that leads to abnormal accumulation of cholesterol and cholesteryl esters and related lipids in macrophages, smooth muscle cell and other types of cells leading to narrowing and/or occlusion of one or several arteries and arterioles of the body and bodily organs, including but not limited to, the coronary arteries, aorta, renal arteries, corotid arteries, and arteries supplying blood to the limbs and central nervous system. The 'associated inflammatory reactions and mediators of this pathologic process also are included in this definition.

As used herein, the term "chronic kidney disease" (CKD) refers to a progressive loss in renal function over a period of months or years. CKD has its general meaning in the art and is used to classify numerous conditions that affect the kidney, destruction of the renal parenchyma and the loss of functional nephrons or glomeruli. It should be further noted that CKD can result from different causes, but the final pathway remains renal fibrosis. Examples of etiology of CKD include, but are not limited to, cardiovascular diseases, hypertension, diabetes, glomerulonephritis, polycystic kidney diseases, and kidney graft rejection.

The term "fragment crystallizable region (Fc region)" refers to the carboxy-terminal region of a heavy chain of an antibody that can interact with cell surface receptors called Fc receptors and some proteins of the complement system.

The term "fusion protein" or "fusion polypeptide" refers to a protein having at least two heterologous polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. As used herein, the term "host cell" refers to a cell or cell line into which a recombinant expression vector for production of a polypeptide may be transfected for expression of the polypeptide.

The term "hypertension" refers to a condition where the pressure of blood within the blood vessels is higher than normal as it circulates through the body. Normal blood pressure at rest is within the range of 100-140 millimeters mercury (mmHg) systolic and 60-90 mmHg diastolic. High blood pressure is present if the resting blood pressure is persistently at or above 140/90 mmHg for most adults.

Hypertension is classified as is classified as "essential" (primary) or "secondary". Essential (primary) hypertension does not have an apparent cause. It may be due to such things as family history or lifestyle. Most people with high blood pressure have essential hypertension. Secondary hypertension, on the other hand, is less common and is the result of another condition, such as: disorders of the adrenal gland including Cushing's syndrome, hyperaldosteronism, and pheochromocytoma; kidney disease, which may include polycystic kidney disease, kidney tumor, kidney failure, or a narrow or blocked main artery supplying the kidney; drugs such as corticosteroids (anti-inflammatory drugs like prednisone), nonsteroidal anti-inflammatory drugs, weight loss drugs (such as phentermine), cold medications that include decongestants such as pseudoephedrine, birth control pills (the estrogen component), and migraine medications; sleep apnea; coarctation of the aorta, a birth defect in which the aorta is narrowed; preeclampsia, a condition related to pregnancy; and thyroid and parathyroid problems.

The term "ischemia" as used herein refers to an inadequate or stopped flow of blood to a part of the body, caused by constriction or blockage of the blood vessels supplying it.

The term "ischemia of the brain" refers to an absolute or relative shortage of the blood supply to the brain, with resultant damage or dysfunction of cerebral tissue, especially central nerve cells.

The term "ischemia of the heart" refers to the reduction of blood flow to cardiac tissue which can result in dysrhythmic conditions, e.g. ventricular arrhythmia and ventricular fibrillation, and cell death. Such dysrhythmic conditions are the result of the asynchronous excitability states created between normal and ischemic-injured cardiac cells which, in turn, caused a disruption of the normal ion transport channels within the cardiac tissue.

As used herein, the term "myocardial infarction" (also known as "heart attack") refers to an acute cardiovascular event that occurs suddenly, when a part of the heart is deprived of blood supply, and is defined by the demonstration of myocardial cell necrosis due to significant and sustained ischemia.

The term "peripheral vascular disease" or "PVD" refers to peripheral atherosclerotic disease or arteriosclerosis obliterans, which involves occlusion of the blood supply to the extremities by atherosclerotic plaques and encompasses intermittent claudication (pain caused by too little blood flow).

The term "phospholipid", refers to compounds derived from fatty acids and a phosphate-containing compound attached to glycerol or the amino alcohol sphingosine, resulting in compounds with fat-soluble and water-soluble regions. The term "lysophospholipid" refers to a derivative of a phospholipid in which one or both acyl groups have been removed by hydrolysis.

The term "preeclampsia", as used herein, refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizure. These conditions usually develop during the second half of pregnancy (after 20 weeks), though they may develop shortly after birth or before 20 weeks of pregnancy.

The term "resistant hypertension" refers to blood pressure that remains above normal despite concurrent use of three antihypertensive agents of different classes, one of which is a diuretic.

As used herein, the term "recombinant protein" refers to a protein produced as the result of the transcription and translation of a gene carried on a recombinant expression vector that has been introduced into a host cell.

The term "reperfusion injury" refers to tissue damage caused when blood flow returns to the tissue after a period of ischemia.

The term "subject" or "patient" refers to an animal including the human species that is diagnosed with a disease and is treated with the methods of the present invention. The term "subject" or "patient" is intended to refer to both the male and female gender unless one gender is specifically indicated.

The term "Sphingosine-1-phosphate" (S1P) refers to a signaling sphingolipid, also known as lysosphingolipid. S1P is also referred to as a bioactive lipid mediator. Sphingolipids at large form a class of lipids characterized by a particular aliphatic aminoalcohol, which is sphingosine. S1P has the following chemical structure:

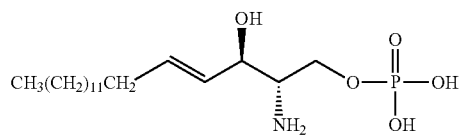

and the chemical name "(2S,3R,4E)-2-Amino-4-octadecene-1,3-diol 1-phosphate, D-erythro-Sphingosine 1-phosphate". S1P can be extracted and purified from tissue samples, cells or plasma from heparanized blood according to protocols known in the art, e.g. the protocol recited in Reimann, C and Gräler, M. H. (*Bio-protocol*, (2016), 6(10): e1817. DOI: 10.21769/BioProtoc.1817). Purified S1P is also available from various commercial sources, e.g., from Sigma-Aldrich (Catalog #:59666), from VWR (Catalog #: AAJ66459-LB0) or from Tocris Bioscience (Catalog #: 1370).

General Description

ApoM-Fc Fusion Proteins

Free ApoM that is not associated with HDL has an extremely short half-life (e.g., an in vivo half-life of less than 15 minutes) (Faber, K. et al., *Molecular Endocrinology*, 20, 212-218, (2006)). In accordance with the present disclosure, the inventors have discovered that the half-life of an Apolipoprotein M (ApoM) protein is significantly increased when it is fused with a fusion partner such as the fragment crystallizable ($F_c$) region of an antibody (e.g., an in vivo half-life of greater than 96 hours). Without being bound to any particular theory, an $F_c$ domain improves the stability of ApoM by preventing its degradation by proteosomes. The ApoM-Fc fusion proteins disclosed herein have been shown to be functional and effective to raise plasma levels of bioactive phospholipids in vivo. The disclosed ApoM-Fc fusion proteins can be recombinantly produced in a highly purified form, and purified ApoM-Fc fusion proteins can be stored in buffered saline solutions for a longer period than a purified native ApoM protein. ApoM fusion proteins can also be used to deliver phospholipids to organs and tissues in need thereof.

Accordingly, in one aspect, this disclosure provides an ApoM-Fc fusion protein. In some embodiments, the ApoM-Fc fusion protein is provided as a dimer. In some embodiments, an ApoM-Fc dimer is formed via disulfide bonding between the Fc regions.

According to this disclosure, "ApoM" in an ApoM-Fc fusion protein refers to any ApoM polypeptide that includes the portion of a native mature ApoM protein that retains the S1P binding ability. In one embodiment, the ApoM polypeptide in an ApoM-Fc fusion protein is a human ApoM polypeptide. In a specific embodiment, the ApoM polypeptide in an ApoM-Fc fusion protein comprises amino acids 21-188 of SEQ ID NO: 9. In some embodiments, the ApoM polypeptide in an ApoM-Fc fusion protein comprises the full length, mature ApoM protein as in SEQ ID NO: 9. In some embodiments, the ApoM polypeptide in an ApoM-Fc fusion protein contains deletions, additions, modification or substitutions of one or more amino acid residues as compared to a native ApoM protein or a native ApoM protein fragment, provided that the ApoM polypeptide retains the S1P binding ability. For example, the ApoM polypeptide in an ApoM-Fc fusion protein has an amino acid sequence that is at least 85%, 90%, 95%, 98%, or 99% identical with SEQ ID NO: 9, or with amino acids 21-188 of SEQ ID NO: 9.

In some embodiments, an Fc region used herein includes at least CH2 and CH3 of an immunoglobulin. In some embodiments, an Fc region includes a hinge, a CH2 domain and CH3 domain of an immunoglobulin. The hinge can serve as a flexible spacer between the two parts of the Fc-fusion protein, allowing each part of the molecule to function independently. In some embodiments, the Fc region in an ApoM-Fc fusion protein is an Fc region of an immunoglobulin selected from of IgG, IgM, IgA, IgE and IgD. In a specific embodiment, the Fc region is an Fc region of IgG1 (IgG1-Fc). In some embodiments, an Fc region is fused to the amino terminus of ApoM; whereas in other embodiments, the Fc region is fused to the carboxyl terminus of ApoM. In some embodiments, an Fc region is fused to an ApoM protein directly, i.e., without a linker. In other embodiments, an Fc region is fused to an ApoM protein through a linker. Any type of linker can be used by the skilled person, provided that said linker allows chemical linkage of the ApoM peptide to the Fc region. Linkers suitable for this disclosure can be short peptide sequences that occur between protein domains. In some embodiments, linkers are composed of flexible residues like glycine and serine so that the adjacent protein domains are free to move relative to one another.

In some embodiments, an ApoM-Fc fusion protein can be recombinantly produced in a suitable host cell. Appropriate host cells include bacteria, archebacteria, fungi, especially yeast, and plant, insect and animal cells, especially mammalian cells. Specific examples of host cells include *E. coli, B. subtilis, Saccharomyces cerevisiae, Saccharomyces carlsbergensis, Schizosaccharomyces pombe, Pichia pastoris*, SF9 cells, C129 cells, 293 cells, Neurospora, and CHO cells, COS cells, HeLa cells, and immortalized mammalian myeloid and lymphoid cell lines. In a specific embodiment, an ApoM-Fc fusion protein can be expressed in *E. coli*, recovered from inclusion bodies, purified (e.g., through chromatography), and refolded, as described by Sevvana et al., (*J. Mol. Biol.* 393: 920-936 (2009)). In another specific embodiment, an ApoM-Fc fusion protein can be expressed in sf9 insect cells infected with a strain of baculovirus comprising an ApoM-Fc fusion protein-encoding nucleic acid construct.

In another embodiment, an ApoM-Fc fusion protein is produced using an in vitro cell-free translation system, available commercially e.g., through Life Technology or any other appropriate source. Both prokaryotic and eukaryotic cell-free translation systems can be used. Typically, a cell-free translation system utilizes extracts prepared from cells engaged in a high rate of protein synthesis, such as rabbit reticulocytes, wheat germ and *E. coli*, which contain the macromolecular components (70S or 80S ribosomes, tRNAs, aminoacyl-tRNA synthetases, initiation, elongation and termination factors, for example) required for translation. The extract is generally supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.). Some translation systems, such as reticulocyte lysates and wheat germ extracts, use RNA as a template, whereas other systems start with DNA templates, which are transcribed into RNA then translated. All these systems are suitable for use in synthesis of an ApoM-Fc fusion protein in vitro.

In some embodiments, an ApoM-Fc fusion protein is purified using a suitable protein purification techniques. In a specific embodiment, an ApoM-Fc fusion protein is purified using chromatography. In some embodiments, ApoM-Fc fusion protein purification comprises at least one of ion exchange chromatography, size-exclusion chromatography or expanded bed adsorption chromatic separation methods. In a specific embodiment, the chromatography method is lectin affinity chromatography, protein A affinity chromatography, gel filtration chromatography, or a combination thereof. In some embodiments, an ApoM-Fc fusion protein can be purified through affinity tag purification. In a specific embodiment, an ApoM-Fc fusion protein can be tagged with a poly-His tag and be purified by Nickel affinity purification. In another embodiment, an ApoM-Fc fusion protein can be tagged with a tag selected from a myc-tag, a FLAG tag, an HA tag, a GST tag, an NE tag, a V5 tag, or a VSV tag or any other tag known in the art and subsequently purified using an antibody against the tag Purity of an ApoM-Fc fusion protein can be assessed by various methods including, but not limited to, SDS-PAGE followed by silver staining, and chromatography and multiwavelength detection as described in Frank J. et al., *Anal Biochem*. April; 162(1):65-73 (1987).

Purified ApoM-Fc fusion proteins can be maintained in buffered saline for in vitro or in vivo use.

In some embodiments, an ApoM-Fc fusion protein may be covalently linked or attached to a carrier or a vehicle to further improve the desired biological qualities of the protein. In a specific embodiment, the desired biological qualities of an ApoM-Fc fusion protein comprise increase of bioavailability, or increase or extension of the plasma half-life of the protein in vivo. In a specific embodiment, the carrier comprises Polyethylene Glycol (PEG) or nanoparticles.

Compositions Comprising a Complex of an ApoM-Fc Fusion Protein with a Phospholipid or a Lysophospholipid This disclosure further provides compositions comprising an ApoM-Fc fusion protein in complex with a phospholipid or a lysophospholipid.

As used herein, a complex forms between the ApoM fusion protein and a phospholipid, wherein the fusion protein binds to (i.e., is bound by) the phospholipid via non-covalent interactions. Phospholipids are naturally insoluble in water and form membranes or micelles in solution. Without being bound to any particular theory, an ApoM-Fc fusion protein increases the solubility of the phospholipids in solution by binding to and masking the hydrophobic portion of the phospholipids. Therefore, an ApoM-Fc fusion protein allows transport of phospholipids in aqueous mediums, such as the blood, thereby acting as a carrier of phospholipids.

In some embodiments, the phospholipid can be selected from phosphatidylcholine, phosphatidylethanolamine, phosphatidylserine, sphingomyelin, or a combination thereof.

In some embodiments, the lysophospholipid of the composition comprises a naturally occurring lysophospholipid, a synthetic lysophospholipid, or a combination thereof. In some embodiments, the lysophospholipid comprises a glycerol backbone to which a polar group (e.g. a phosphocholine group) is bound, a free hydroxy group in position 2 of the glycerol backbone and a saturated or unsaturated fatty acid residue attached to the glycerol backbone. In some embodiments, the fatty acid residue of the lysophospholipid has a $C_n$-alkyl chain or a $C_n$-alkenyl chain, wherein n>4. In a specific embodiment, the lysophospholipid comprises an oxidized fatty acid residue.

In some embodiments, a complex between an ApoM-Fc fusion protein with a phospholipid or a lysophospholipid can be formed by mixing the fusion protein with the phospholipids or the lysophospholipids suspended in methanol, beta-cyclodextran or DMSO. In some embodiments, the fusion protein is mixed with a lipid at a ratio of about 1:2 to 1:50 (mole fusion protein/mole phospholipid or lysophospholipid). In some embodiments the ratio of (mole fusion protein/mole phospholipid or lysophospholipid) in methanol beta-cyclodextran or DMSO is about 1:2, 1:3, 1:4, 1:5, 1:6, 1:7, 1:8, 1:9, 1:10, 1:20, 1:30, 1:40 or 1:50. In a specific embodiment, said ratio is 1:8. A fusion protein-lipid mixture can be incubated for 24-48 hours at about 4-37° C. In some embodiments, the incubation temperature is at about 2° C., 4° C., 10° C., 15° C. 20° C., 25° C., 30° C., 35° C., or 40° C. In some embodiments, the incubation time is about 24 hours, 30 hours, 36 hours, 42 hours or 48 hours.

An ApoM-Fc fusion protein/phospholipid or lysophospholipid complex can be purified to remove free/unbound lipids using known techniques, e.g., chromatography. In specific embodiments, the purification of an ApoM-Fc fusion protein—phospholipid complex comprises at least one of ion exchange chromatography, size-exclusion chromatography or expanded bed adsorption chromatic separation methods. In some embodiments, the complex can be purified using an FPLC (Fast Protein Liquid Chromatography) machine. In a specific embodiment, the chromatography method is lectin affinity chromatography, protein A affinity chromatography, protein G affinity charomatography or gel filtration chromatography.

The purified ApoM-Fc fusion protein-phospholipid or lysophospholipid complexes can be analyzed for lipid content by liquid chromatography/mass spectroscopy (LC/MS/MS) as described in Sommer, U. et al. (*Journal of Lipid Research*, 47(4), 804-814 (2006)) and Christoffersen, C. et al. (*PNAS*, 108, 9613-9618, (2011)).

In some embodiments, S1P binding to ApoM-Fc fusion protein can be determined by intrinsic tryptophan fluorescence quenching in a fluorescence spectrophotometer as previously described (Sevvana, M. et al., *Journal of Molecular Biology*, 404, 363-371 (2010)).

In some embodiments, after purification to remove unbound lipids, the resulting composition includes ApoM-Fc fusion proteins bound with lipids (i.e., a complex, or "loaded"), as well as ApoM-Fc fusion proteins that are not bound by lipids ("unloaded"). In some embodiments, at least about 30%, 35%, 40%, 45%, 50%, 55%, 60%, 65%, 70%, 75%, 80%, 85%, 90%, 95%, 99% or more of the ApoM-Fc fusion proteins within a composition are bound by phosholipid or lysophospholipid. The percentage of ApoM-Fc fusion proteins within a composition that are bound by phosholipid or lysophospholipid can be determined by mass spectroscopy, e.g. using electrospray ionizing-tandem mass spectrometry (ESI-MS/MS).

In some embodiments, within ApoM-Fc fusion protein-phospholipid or lysophospholipid complexes, the ratio of a ApoM-Fc fusion protein to phospholipid or lysophospholipid is about 1:0.3, 1:0.4, 1:0.5, 1:0.6, 1:0.7, 1:0.8, 1:0.9 or 1:1. The ApoM-Fc fusion protein: phospholipid or lysophospholipid ratio in fusion protein-lipid complexes can be determined by mass spectroscopy, e.g. using electrospray ionizing-tandem mass spectrometry (ESI-MS/MS).

Pharmaceutical Compositions

Pharmaceutical compositions containing an ApoM-Fc fusion protein, with or without phospholipid bound thereto, may be prepared using one or more physiologically acceptable carriers or excipients. As used herein, a pharmaceutically acceptable carrier includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof. In some embodiments, the carrier is a controlled release matrix, a material which allows the slow release of the active ingredients in ApoM-Fc fusion-containing compositions.

In accordance with the present invention, the active ingredients of the present pharmaceutical compositions can be combined with a carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. When appropriate, the pharmaceutical compositions of the present invention should be made sterile by well known procedures. For example, solutions can be made sterile by filter sterilization or autoclave. To obtain a sterile powder, sterilized solutions can be vacuum-dried or freeze-dried as necessary.

Methods of Treatment

In one aspect, this disclosure provides methods of treating a condition in a subject, wherein the condition would benefit from an increase plasma levels of phospholipids, comprising administering the subject a pharmaceutical composition comprising an ApoM-Fc fusion protein in complex (or bound) with a phospholipid. The Administration of the pharmaceutical composition leads to the delivery of bioactive phospholipids in the complex to endothelial cells and to all tissues of the body. The delivered bioactive phospholipids in turn promote endothelial function compromised in disease including, but not limited to, cardiovascular, inflammatory and metabolic diseases In some embodiments, the phospholipid is a sphingolipid. In a specific embodiment, the sphingolipid is sphingosine 1-phosphate (S1P).

In some embodiments, the subject is suffering from a condition that is selected from the group consisting of hypertension, ischemia of the heart, ischemia of the brain, accelerated atherosclerosis, non-cardiac reperfusion injury and peripheral vascular disease, which are among diseases that would benefit from an increase in plasma levels of phospholipids. In specific embodiments, the hypertension comprises conditions selected from the group consisting of primary resistant hypertension, secondary resistant hypertension, neurogenic hypertension, gestational hypertension (pre-eclempsia), diabetic pre-eclempsia, and hypertension of chronic kidney disease. In some embodiments, the ischemia of the heart comprises diseases selected from the group consisting of cardiac reperfusion injury, myocardial infarction, acute coronary syndrome and angina. In some embodiments, the non-cardiac reperfusion injury comprises an injury as a result of an ischemia to an organ or tissue other than the cardiac tissue (the heart). Examples of non-cardiac ischemia include liver ischemia, kidney ischemia, intestinal ischemia, and muscle ischemia.

In other embodiments, the ApoM-Fc fusion protein in a pharmaceutical composition for administration is "unloaded", i.e., not bound by a phospholipid, and recruits and forms complex with circulating S1P in the recipient after administration. Plasma S1P is derived from several cellular sources (Pappu et al., *Science* 316: 295-298 2007). For example, S1P is stored in relatively high concentrations in human platelets, which lack the enzymes responsible for its catabolism, and is released into the blood stream upon activation of physiological stimuli, such as growth factors, cytokines, and receptor agonists and antigens.

In a specific embodiment, an ApoM-Fc fusion protein is given to a patient undergoing a treatment with FTY720/Fingolimod/Gilenya™ (IUPAC name 2-amino-2-[2-(4-octylphenyl)ethyl]propane-1,3-diol) or analogs thereof for an autoimmune disorder. FTY720/Fingolimod/Gilenya™ is an approved therapeutic for multiple sclerosis and may be useful for treating other autoimmune indications such as psoriasis, rheumatoid arthritis, uveitis and type I diabetes. The most common side effects of fingolimod have been head colds, headache, and fatigue. However, Fingolimod has been associated with potentially fatal infections, bradycardia, skin cancer, and a case of hemorrhaging focal encephalitis, an inflammation of the brain with bleeding. In accordance with this invention, it is believed that the side effects of Fingolimod and its analogs can be reduced by the administered ApoM-Fc fusion protein, which will sequester the excess circulating S1P molecules.

The pharmaceutical compositions of the present invention, both the compositions comprising an unloaded ApoM-Fc fusion protein and compositions comprising an ApoM-Fc fusion protein/phospholipid complex, can be administered to a subject by standard routes, including the oral, nasal, intratracheal, transdermal, parenteral (e.g., intravenous, intraperitoneal, intradermal, subcutaneous or intramuscular) or rectal route. In addition, an ApoM-Fc fusion—containing composition can be introduced into the body, by injection or by surgical implantation or attachment, proximate to a preselected tissue or organ site such that a significant amount of the active ingredients is able to enter the site, e.g., in a controlled release fashion, by direct diffusion.

The dosage depends on the disease state or condition being treated and other clinical factors, such as weight and condition of the subject, the subject's response to the therapy, the type of formulations and the route of administration. The precise dosage to be therapeutically effective and non-detrimental can be determined by those skilled in the art. Generally speaking, a pharmaceutical composition can be administered at about 0.5 µg to about 2 grams per unit dosage form. A unit dosage form refers to physically discrete units suited as unitary dosages for mammalian treatment: each unit containing a pre-determined quantity of the active material calculated to produce the desired therapeutic effect in association with any required pharmaceutical carrier. The methods of the present invention contemplate single as well as multiple administrations, given either simultaneously or over an extended period of time.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Creation of ApoM-Fc and Triple-Mutant ApoM-Fc (ApoM-Fc-TM)

The ApoM-IgG1-Fc fusion protein was created by cloning a PCR-derived cDNA corresponding to the $\Delta_{1\text{-}20}$ApoM Open-Reading Frame (ORF) (Xu, N., *JBC*, 274, 31286-31290 (1999)) into the pFUSE-mIgG1-Fc2 vector (InVivogen; Cat. #pfu se-mglfc 2), between the IL-2 signal peptide and the IgG1-Fc framework region. Thus, the 507 bp open reading frame of human ApoM lacking a signal peptide and substituting the stop codon was generated by PCR using the primers:

Fwd:
(SEQ ID NO: 1)
5'-TAT*CCATGG*GGATCTACCAGTGCCCTGAGCACAGT-3'

Rev:
(SEQ ID NO: 2)
5'-TAT*GGATCC*TCCGTTATTGGACAGCTCACAGGCCT-3'

The forward primer inserts a novel NcoI restriction site (bold and italicized) begins at ApoM codon 21 and eliminates the uncleavable ApoM signal peptide23. The reverse primer inserts a novel BamHI restriction site (bold and italicized) and replaced the stop codon (TGA, codon 189) with a glycine codon by an A>G substitution TGA>GGA. The resulting PCR-derived DNA was purified and cleaved by double-digestion with NcoI-BamHI (New England Biolabs; Cat #R0193S, R3136S) and ligated (Quick Ligation Kit, New England Biolabs, Cat #M2200) into the open reading frame of the pFUSE-mIgG1-Fc2 vector (InVivogen; Cat. #pfuse-mglfc2) digested with NcoI-BglII (New England Biolabs; Cat #R0193S, R0144S). BglII is a compatible sticky end for BamHI and upon ligation eliminates both sites. The ligation was transformed into high efficiency transfection competent DH5α (ThermoFisher Scientific; Cat #18263012) and selected on Zeocin (25 µg/ml; ThermoFisher Scientific; Cat #R25005) Miller's broth agar petri plates. Individual colonies were picked and grown in 2 ml of Zeocin (25 µg/ml) Miller's Broth and DNA was isolated using the GeneJET Plasmid Miniprep Kit (ThermoScientific, Cat #K0503). Recombinant vectors were identified using a diagnostic EcoRI (New England Biolabs, R3101S) DNA digest, which releases a 430 bp DNA fragment and positive clones were sequenced using the Cornell DNA sequencing Core Facility. This cloning resulted in the fused gene ApoM-$F_c$ (pApoM-$F_c$). In order to create a non-S1P-binding negative control for these studies, an ApoM-$F_c$ Triple Mutant (pApoM-$F_c$-TM) was created based on the crystallographic analysis of ApoM13. Mutations were created by site-directed mutagenesis at codons R98A, W100A, and R116A using the QuikChange II XL Site-Directed Mutagenesis Kit following the manufacturer's protocol and using the following primers:

```
For R98A and W100A:
                              (SEQ ID NO: 3)
5'-CGCCCTGCCATGGCGACTGAGCTC-3'

For R116A:
                              (SEQ ID NO: 4)
5'-AATCATGCTGAATGCGACAGGCC-3'
```

Mutated plasmids were transformed into bacteria as above and selected on Zeocin agar plates. Clones were isolated and subjected to miniprep as above and sequenced as above. This resulted in the mutant fused gene ApoM-$F_c$-TM (pApoM-$F_c$-TM).

Expression of ApoM-$F_c$, ApoM-$F_c$ TM and IgG-$F_c$1 proteins in Baculovirus.

In order to produce milligram quantities of properly folded, glycosylated protein for in vivo studies, the Bac-to-Bac Baculovirus Expression System (ThermoFisher/Invitrogen) was employed, which uses recombinant baculovirus to express soluble protein in insect cell supernatant. Using the pApoM-Fc, pApoM-Fc Triple Mutant or the original pFUSE-IgG1$F_c$2 (IgG1-$F_c$ alone) plasmids as templates, a further round of PCR was performed using primers reactive to the pFUSE-IgG1F2 vector:

```
Fwd:
                              (SEQ ID NO: 5)
5'-TATGGATCCATGTACAGGATGCAACTCCTGTCTT-3'

Rev:
                              (SEQ ID NO: 6)
5'-TATTTATCATGTCTGGCCAGCTAGCGACACTGGG-3'
```

The forward primer creates a restriction site for BamHI (italicized) and the reverse primer creates a restriction site for NheI (italicized). The resulting PCR-derived DNA cassettes were purified and cleaved by double digestion with BamHI-NheI (New England Biolabs, Cat #R3136S, R5131S) and ligated into the baculovirus expression vector, pFASTBAC1 (Invitrogen), which was restriction digested with BamHI-XbaI (New England Biolabs, R3136S, R5145S). Recombinant viral DNA was generated using the manufacturer's protocol (Invitrogen; Bac-to-Bac Baculovirus Expression System) using DH10BAC1 E. coli bacteria and triple drug selection using Tetracycline (10 µg/ml), Gentamycin (7 µg/ml) and Kanamycin (50 µg/ml) on Luria Broth (LB) agar plates. Individual colonies were selected and grown in LB broth supplemented with the same triple drug combination. Recombinant plasmids were isolated by mini-prep as above and positive clones were sequenced at the Cornell University Sequencing Core Facility. The resulting baculovirus plasmids were termed pApoM-$F_c$ (Bac), pApoM-$F_c$ TM (Bac), or pIgG1-$F_c$ (Bac).

Production of ApoM-$F_c$, ApoM-$F_c$ TM and IgGl-$F_c$ in HEK293T Cells pApoM-$F_c$, pApoM-Fc-TM or the control pFUSE-mIgG1Fc2 vectors were assayed for protein expression by transfection of HEK 293T cells (AATC Cat. #: CRL-1573), using the Lipofectamine2000 reagent (ThermoFisher Scientific, Cat #11668019). Normal cultures were maintained in at 37° C. in DMEM supplemented with 10% Fetal Bovine Serum (FBS). Recombinant pApoM-$F_c$ plasmids were transfected into 3 separate cultures of 293T cells using Lipofectamine 2000 for 72 hours. For the final 18 hours, culture media was replaced with serum free OptiMem media (ThermoFisher Scientific Cat #31985-070). Supernatants were collected, clarified by centrifugation and stored at −80° C. until use.

Production of recombinant ApoM-$F_c$, ApoM-$F_c$-TM, or IgG1-$F_c$ Baculovirus

Recombinant Baculoviral DNA (1-3 µg) pApoM-$F_c$ (Bac), pApoM-$F_c$-TM (Bac), or pIgG1-$F_c$ (Bac) was transfected into individual cultures of the insect cell line Sf9 by the calcium phosphate method provided by the manufacturer. After 5 days, the resulting culture supernatant containing viral particles was passaged onto nave Sf9 cells at 1:50 dilution and incubated for 5 days. This was repeated 3 times to create a high-titer viral stock (>$10^9$ PFU/ml). For further amplification/maintenance of viral stock, $3\times10^7$ Sf9 cells into 150 mm$^3$ tissue culture plates in complete culture medium (Sf900-III; ThermoFisher Scientific, Cat.#12658027) were infected with 500 µl of virus suspension from serial viral amplification steps (passage 5) and incubated for 5 days at 27° C. For protein production, $3\times10^7$ High-Five™ ThermoFisher Scientific, Cat #PHG0143) cells were seeded into 150 mm$^2$ tissue culture plates in complete culture medium (Sf900-III; ThermoFisher Scientific, Cat #12658027) and then infected with 1 ml of viral stock and incubated for 4-5 days at 27° C. in a humidified incubator. Supernatants were collected and clarified by centrifugation at 3,000×g for 10 minutes and stored at 4° C.

Immunoblot Analysis of Recombinant ApoM-Fc

The identity of the fusion proteins was confirmed using anti-ApoM specific immno blot analysis. For most experiments, 10-20 µl of recombinant cell culture supernatant was heated to 95° C. for 10 minutes in 5× Laemmli's sample buffer. Separate samples were prepared either with or without 100 mM Dithiothreitol (Sigma-Aldrich). Samples were separated on a 12% SDS-PAGE gel (BioRad, Acrylamide, Cat #1610156) and transferred electrophoretically to nitrocellulose membrane (BioRad, Cat #1620115). Blots were blocked in 5% milk (Carnation) suspended in TBS-T (50 mM Tris base pH 8.0, 150 mM NaCl, 0.05% Tween-20) for 1 hour at RT and then incubated with a Rabbit anti-ApoM monoclonal antibody (Genetex GTX62234; Clone EPR2904) overnight (>12 hours) and washed with 5 changes of TBS-T over the course of 30 minutes. Blots were incubated in the 1% milk-TBS-T supplemented with Goat anti-Rabbit IgG coupled to Horse Radish Peroxidase (HRP) (1:5000 (v/v); Jackson Labs) for 60 minutes and then washed 5 times over the course of 30 minutes in TBS-T at RT with gentle rocking. Blots were incubated with Immobilon Western Chemiluminescent HRP Substrate Millipore, Cat #WBKLS0500) and chemiluminescence was revealed using X-ray film (Denvillie Scientific, HyBlotCL E3018).

Purification of ApoM-Fc, ApoM-Fc-S1P, ApoM-Fc-TM, and IgG1-Fc

Large-scale purification of fusion proteins was performed on a BioRad NGC FPLC Chromatography System using the following protocol:

Step 1) 100-200 ml of culture supernatant containing the fusion protein was clarified by ultracentrifugation at 42,000 RPM (>100,000 g; Sorvall Discovery 90, T-1250 Rotor) in sterilized polystyrene screw cap tubes.

Step 2) Supernatant was collected and concentrated to 1/10th volume using Amicon Ultra-15 Centrifugal filters (Ultracel-50K).

Step 3) Concentrated culture supernatant was replaced with 10 volumes of Concanavalin A Lectin binding buffer (LBB) (Tris-HCl, 50 mM pH 7.5, NaCl 300 mM, $MnCl_2$ 1.5 mM, $CaCl_2$ 1 mM, $MgCl_2$ 1 mM) in Amicon Ultra-15 Centrifugal filters (Ultracel-50K).

Step 4) The protein sample was applied to a 5 ml Bioscale MT-5 column of pre-packed Concanavalin A-Sepharose beads previously washed with 20 bed volumes of LBB. The application rate was 0.2 ml/minute with an average pressure of 30 psi.

Step 5) The column was washed with LBB at a flow rate of 0.4 ml/minute until column flow-through reached buffer baseline $OD_{280}$-typically 55-57 mAU.

Step 6) Proteins were eluted off the column using LBB supplemented with 200 mM α-methyl-mannoside (elution buffer), which was filter-sterilized before use. After subtracting system volume, typically, 2 ml of elution buffer was applied to the column (0.4 ml/minute) and then incubated for 15-30 minutes in order to allow efficient displacement of bound proteins.

Step 7) Proteins were eluted off the column in elution buffer at a rate of 0.4 ml/minute. 0.8 ml fractions were collected on a BioFrac collector until $OD_{280}$ returned to elution buffer baseline (~125 mAU).

Step 8) Positive fractions were pooled and concentrated 10-fold on an Amicon Ultra-4 Centrifugal Filter (Ultracel-10K) and elution buffer was replaced with 10 volumes of PBS-1 mM EDTA to remove mannose.

Step 9) The approximate concentration of fusion protein was determined by BCA protein analysis (ThermoFisher Scientific) of the sample combined with SDS-PAGE of 5 µg of the preparation. For some experiments, fusion protein was mixed with S1P re-suspended in Methanol in 1:8 (mole fusion protein/µmole S1P) and incubated for 24-48 hours at 4° C. with gentle rocking. The final concentration of methanol in the sample did not exceed 3% (vol/vol). The sample was concentrated on an Amicon Ultra-4 Centrifugal Filter (Ultracel-10K).

Step 10) 1 ml of protein concentrate was injected onto a Superose 6 Increase 10/300 GL column pre-equilibrated with PBS-1 mM EDTA and separated at a rate of 0.4 ml/l minute until peak fractions were collected.

Step 11) Protein positive fractions were pooled and concentrated in an Amicon Ultra-4 Centrifugal Filter (Ultracel-10K). Buffer was replaced with 10 volumes of sterile PBS and maintained at a final concentration of 1-3 mg/ml.

Analysis of FPLC Protein Fractions

All fractions were analyzed by SDS-PAGE. 10 µl of each fraction was boiled at 95° C. in 5X Laemmli's sample buffer supplemented with 100 mM DTT and separated on a 12% SDS-PAGE gel. Gels were fixed in Methanol:Acetic Acid:water (50%:10%:40%) and stained in fixative solution containing 0.3% Coomassie Brilliant Blue (BioRad) and destained in fixative solution.

Measurement of ApoM-$F_c$ Binding of S1P Based on Fluorescence Quenching Analysis Previous studies had demonstrated that bacterially expressed recombinant ApoM binds to S1P with a relative affinity of ~1 µM, based on fluorescence quenching of tryptophan 47 (W47) of the predicted human ApoM polypeptide (Sevvana, M. et al., *Journal of Molecular Biology*, 404, 363-371 (2010)). Thus, 0.125, 0.25 and 0.5 µM of ApoM-Fc, ApoM-$F_c$-TM, or IgG1-$F_c$ were analyzed for lipid-dependent fluorescent quenching on a Quantamaster300™ (Horiba) collecting emission spectra collecting a range of 250-400 nm. Baseline emission was established and the emission maxima were determined for each protein sample. For quenching studies, each protein was stabilized for 5 minutes and then S1P dissolved in methanol was added to a final concentration of 0.25-3.0 µM over the course of 60 minutes. Since fusion protein was being evaluated and the interest is only in quenching in ApoM, IgG1-$F_c$ was used as a control for non-specific quenching of the carboxy-terminus of the fusion protein. Emission fluorescence of IgG1-Fc was subtracted from all appropriate ApoM-$F_c$ and ApoM-$F_c$-TM data. Data were collected and analyzed using FelixGX software.

Measurement of S1P in Purified ApoM-$F_c$ ApoM-$F_c$-TM or Blood Plasma After Injection of ApoM Fusion Proteins.

50 µg of purified ApoM-$F_c$, ApoM-$F_c$-S1P, ApoM-$F_c$-TM or ApoM-$F_c$-TM were analyzed for sphingolipid content by liquid chromatography/mass spectroscopy (LC/MS) using the Stony Brook University Lipidomics Core Facility. For plasma studies, Apom$^{-/-}$ or C57BL/6 mice were pre-bled for by the cheek punch method and allowed to rest for 24-48 hours. Mice were injected IP with 100 µg (4 mg/kg) of Apom-$F_c$-S1P or ApoM-$F_c$-TM and after 24 hours blood was collected in EDTA and centrifuged at 2000×g for 10 minutes to collect plasma. 25 µl of plasma was analyzed for sphingolipid content and species by LC/MS.

In Vitro Analysis of S1P Dependent Signal Transduction in $S1P_1$ Reporter Cells Proia and colleagues established the mouse strain, based on the β-arrestin signaling to record $S1P_1$ signaling (called $S1P_1$ GFP signaling mouse) (Kono, M. et al., *JCI*, 124, 2076-2086 (2014)). Essentially, activation of the $S1P_1$ receptor by S1P results in accumulation of a Histone-GFP fusion protein in the nuclei of activated cells. A mouse embryonic fibroblast (MEF) cell line was established from day 10.5 embryos. Using standard protocols, embryos were dissociated, MEF cells were isolated and transformed with SV40 Large T antigen. Resulting transformed cells were selected for low endogenous GFP expression and were maintained in DMEM supplemented with 10% charcoal-stripped Fetal Bovine Serum, which contains very low levels of S1P. For functional assays, it was determined that addition of Fatty Acid Free (FAF) albumin-S1P (Alb-S1P) results in nuclear GFP accumulation, appearing as early as 6 hours with maximum signal at 24 hours post stimulus. Treated cells were harvested by trypsinization and directly analyzed by FACS analysis, gating on GFP expression. Using this assay, 0.12-1 µM of ApoM-Fc-S1P or ApoM-Fc-TM was assayed for in $S1P_1$ activation and GFP expression by FACS analysis. Data were expressed as a % GFP positive/Total live cells analyzed.

Analysis of the Effect of ApoM-$F_c$ or ApoM-$F_c$-TM on Signal Transduction Through S1P Receptors 1, 2, and 3.

It was previously reported the analysis of S1P receptor-1 signaling in stably transfected Chinese Hamster Ovary (CHO) cells, using $S1P_1$ cDNA cloned into the lentiviral vector, p (CHO-$S1P_1$) (Christoffersen, C. et al., PNAS, 108, 9613-9618 (2011)). Separate CHO cell clones were established for S1P receptor-2 using the Tet-On vector system (CHO $S1P_2$). Cells were maintained in Ham's F12 media (Invitrogen) supplemented with 10% FBS. For analysis of signal transduction, seeded cultures were allowed to adhere overnight, washed twice in serum-free media and then cultured overnight in media supplemented with 0.1% FAF-Albumin. Media was replaced and cells were incubated for 5 minutes with OptiMem media alone or Albumin-S1P (100 nM S1P), ApoM-$F_c$-S1P, or ApoM-$F_c$-TM. Cells were washed briefly with PBS and then lysed in PBS-NP-40 (PBS, 1% NP40, Protease inhibitors (Sigma), and 1 mM of NaVO3, 10 mM NaF, 10 mM β-glycerol Phosphate). Lysates were clarified by centrifugation for 10 minutes at 4° C. at 13,000 g and supernatants were mixed with 5× Laemmli's buffer containing 100 mM DTT. Samples were separated on a 12% SDS-PAGE gel (BioRad, Acrylamide, Cat. #1610156) and transferred electrophoretically to nitrocellulose membrane (BioRad, Cat. #1620115). Blots were blocked in 5% milk (Carnation) suspended in TBS-T (50 mM Tris base pH 8.0, 150 mM NaCl, 0.05% Tween-20) for 1 hour at RT and then incubated with a Mouse monoclonal antibody for p-p44/42 MAPK (T202/Y204) ((E10) 9106S, Cell Signaling), 1:1000 overnight (>12 hours) and washed with 5 changes of TBS-T over the course of 30 minutes. Blots were incubated in the 1% milk-TBS-T supplemented with Goat anti-Mouse IgG coupled to Horse Radish Peroxidase (HRP) (1:5000; Jackson Labs) 60 minutes and then washed 5 times over the course of 30 minutes in TBS-T at RT with gentle rocking. Blots were incubated with Immobilon Western chemiluminescent HRP Substrate (Millipore, Cat #WBKLS0500) and chemiluminescence was revealed using X-ray film (Denvillie Scientific, HyBlotCL E3018). As a loading control, blots were stripped using glycine pH 2.5 for 10 minutes and re-probed with Rabbit anti-ERK1/2 (Santa Cruz Biotechnology, Cat #sc-292838). Blots were stripped and re-probed for expression of pAkt (S473) (#9271L Cell Signaling) and total Akt (#9272S, Cell Signaling). Blots were incubated, washed and developed as described above.

HUVEC (ATCC Cat. #100-010) were maintained in supplemented EGM buffer and split prior to assay. Cells were starved in 0.1% FAF-Albumin media for 4 hours and then assayed. For signaling experiments, starved cells were cultured at 5, 15 or 30 minutes with Alb-S1P (100-400 nM S1P), ApoM-$F_c$-S1P (5-20 µg/ml), or ApoM-$F_c$-TM (5-20 µg/ml). Cells were lysed, lysates were separated and transferred for Western Blotting as described above. In addition to MapK and Akt, blots were analyzed for activation of p-eNOS (s1177) (#9571S Cell Signaling) and total eNOS expression (cat #610296, BD Biosciences).

Generation of S1P1-Knockout HUVEC by CRISPR/Cas9

Guide RNA (gRNA) targeting the S1PR1 starting codon was designed and cloned into the lentiCRISPRv2 vector (a gift from Dr. Feng Zhang, Addgene plasmid #529619) using the following oligonucleotides:

```
                                       (SEQ ID NO: 7)
5'-CACCGCGGGACGCTGGTGGGCCCCA-3'
and (SEQ ID NO: 8)
5'-AAACTGGGGCCCACCAGCGTCCCGC-3'.
```

The lentiviral particles were prepared using HEK 293T cells and infected into HUVECs. Forty-eight hours after infection, 2 µg/ml of puromycin was added for selection, HUVEC were analyzed for the mutation of the S1PR1 locus by DNA sequencing and S1P1 protein expression was determined by immunoblot analysis.

Measurement of $S1P_1$ Internalization

The human osteosarcoma cell line, U2OS, was created to stably express the $S1P_1$ receptor fused to GFP and selected for high-level expression. Cells were plated in a 384 well plate and brought to confluence. Cells were then starved in serum-free media for 2 hours and individual wells were stimulated for 30 minutes with several concentrations of FTY720-P, Albumin-S1P (10-100 nM), ApoM-$F_c$-S1P (1-20 µg/ml ) or ApoM-$F_c$-TM (1-20 µg/ml). Cells were then fixed for 15 minutes with 4% PFA and permeabilized 10 minutes in PBS-0.1% Triton. Nuclei were stained with DAPI for 5 minutes. Cells were maintained in PBS, imaged in 384 well plates by an ArrayScan VTI at 10× using the spot detector software.

Measurement of Endothelial Cell Barrier Function in Vitro \

Human umbilical vein endothelial cells (HUVECs) were maintained under standard conditions and analyzed between passages 4 and 8. Endothelial barrier function was evaluated by measuring the resistance of a cell-covered electrode by using and endothelial cell impedance system (ECIS) instrument (Applied BioPhysics, Troy, N.Y., USA). HUVECs were plated on 0.1% fibronectin—coated electrodes (8W10E plates) at the density of $1 \times 10^5$ cells/well (Kono, M. et al., JCI, 124, 2076-2086 (2014)). Confluent cells were starved for 2-6 h in endothelial basal medium (EBM-2; Lonza, Basel, Switzerland) and treated with either Albumin-S1P (50-200 nM; S1P was dissolved in 2% fatty acid-free Albumin; Sigma-Aldrich), ApoM-$F_c$-S1P, or ApoM-$F_c$-TM (both 0.2-0.4 µM). Resistance was monitored and expressed as fractional resistance, normalizing to the baseline at the initiation of the assay.

Mice and Cell Lines

C57B1/6 male mice (6-8 weeks old) were purchased from Jackson Labs. ApoM knockout mice in the C57B1/6 background were maintained as previously reported (Christoffersen, C. et al., PNAS, 108, 9613-9618 (2011)). All animal protocols were approved by the Institutional Animal Care and Use Committee (IACUC) of Weill-Cornell Medicine. All cell lines were tested for mycoplasma contamination.

Measurement of the Plasma Half-Life of ApoM-$F_c$ or ApoM TM in C57B1/6 mice.

6-8 week-old C57B1/6 mice (n=4) were administered (i.p.) 100 µg (4 mg/kg) of either purified ApoM-$F_c$ or ApoM-$F_c$-TM and were analyzed at 2, 4, 6, 8, 24, 48, 72, 96, 120, 168, and 216 hours post injection. 1 µl of plasma was analyzed by SDS-PAGE and anti-ApoM immunoblot analysis as described above. Ponceau S staining was performed to establish that loading per lane was equivalent. Scans of western blots were quantified for protein expression by ImageJ analysis using un-injected plasma as a control.

Maximum signal was observed between 4-6 hours and this was used as the reference point for evaluating subsequent expression at various time points.

Effect of ApoM-$F_c$ Administration on Blood Cell Counts in WT Mice.

C57Bl/6 WT mice were injected with 100 µg (4 mg/kg) of ApoM-$F_c$-S1P, or ApoM-$F_c$-TM or PBS (N=5 for each) by intra-peritoneal injection. After either 6 or 24 hours, blood was harvested into 2 mM EDTA and the cellular fractions were separated by centrifugation. Total blood counts were determined by Clinical Cytometry (Cytometry Core, Memorial Sloan-Kettering Cancer Center).

Analysis of the Effect of ApoM-$F_c$ and ApoM-$F_c$ Triple Mutant on Systolic Blood Pressure (SBP) in Normotensive Mice.

Systolic, diastolic and mean blood pressure was measured in conscious 12-week-old male mice using the pneumatic tail-cuff method (MRBP System, Life Science, Woodland Hills, Calif.). Briefly, animals were placed in a plastic chamber maintained at 34° C. and a cuff with a pneumatic pulse sensor was attached to the tail. After 1 week of training, multiple measurements were performed per mouse, and the values were averaged. Mice were given intraperitoneal injections of PBS (vehicle control), ApoM-$F_c$-S1P or ApoM-$F_c$-TM (4 mg/kg) and blood pressure was monitored at 1, 2, 4, 8, and 24 hours and then every 24 hours until day 7.

Chronic Infusion of AngII and Analysis of the Effect of ApoM-$F_c$ and ApoM-$F_c$ Triple Mutant on Hypertension.

AngII (500 ng/kg/min) was infused using an osmotic mini-pump (model ALZET 2004) as described previously (Cantalupo, A. et al., Nature Medicine, 21, 1028-1037, (2015)). Briefly, mini-pumps were implanted subcutaneously in C57B1/6 (WT), male mice at 10 weeks of age. Blood pressure was monitored twice per week from day 0 to day 14 of AngII infusion. Systolic Blood Pressure was evaluated as described above. In another set of experiments, C57B1/6 mice were treated by I.P. injection with PBS (vehicle control) or 100 µg (4 mg/kg) of either ApoM-$F_c$ or ApoM-$F_c$-TM suspended in PBS and blood pressure was measured at different time points (1 hour to 216 hours) post-injection. To determine dose response relationships, a similar experiment was performed using PBS (vehicle control) or 30 µg (1.3 mg/kg) of either ApoM-$F_c$ or ApoM-$F_c$-TM suspended in PBS. In addition, S1P receptor-1 antagonist W146 (10 mg/kg) (8) was used in similar experiments. W146 was administered by intra-peritoneal injection at time 0, and then at 24-hour intervals (24-96 hours, and then again at 168 hours).

Measurement of Plasma Nitrite in AngII Treated Mice After ApoM-$F_c$-S1P or ApoM-$F_c$-TM NO levels were measured as nitrite in plasma from AngII-treated WT mice, 24 hours post infusion with ApoM-$F_c$-S1P or ApoM-$F_c$-TM, using a modified Griess reaction as described previously (Cantalupo, A. et al., Nature Medicine, 21, 1028-1037 (2015)). Briefly, after precipitation of plasma proteins with $ZnSO_4$ (30% w/v), supernatants were chemically reduced with acid-washed (0.24 M HCl) cadmium powder (Sigma-Aldrich). After centrifugation, samples were measured for nitrite content with Griess reagent (0.1% naphtylethylendiamine dihydrochloride in $H_2O$ and 1% sulfaniamide in 5% concentrated $H_3PO_4$) and read at a wavelength of 550 nm. All samples were assayed in duplicate and the NO concentration was calculated against a $NaNO_2$ calibration curve.

Myocardial Ischemia/Reperfusion (MI/R) In Vivo.

A model for Myocardial Ischemia Reperfusion (MI/R) injury was employed as previously reported (Xu, Z., JoVE, doi:10.3791/51329 (2014)). Essentially, mice were anesthetized, thoracic cavity is opened by a small incision between the ribs and the heart is exposed. The Left Anterior Descending Artery (LAD) of the heart is identified and compressed by a slipknot suture ligation. After 45 minutes, the slipknot is removed and the incision is closed. After 24 hours, the mice are sacrificed. To visualize the area at risk (AAR), the heart was perfused with Alcian blue dye via the aorta and coronary arteries and the extent of infarction is evaluated by microscopic analysis of 1 mm transverse sections of the heart. The heart was counterstained with 1% triphenyltetrazolium chloride (TTC) solution for 15 minutes. Images were visualized by light microscopy and photographed. The infarct area and the AAR (non blue) and the total Left Ventricle (LV) were evaluated after ImageJ analysis and expressed as the percentage of infarcted area (no Alcian blue perfusion)/total cardiac area below the suture ligation (Shao, D. et al., Nature Communications, 5, 3315 (2014)). For all experiments, 30 minutes prior to surgery, WT C57B1/6 mice were dosed with 100 µl IV by retro-orbital injection with 4 mg/kg of ApoM-$F_c$-S1P or ApoM-$F_c$-TM.

Immunofluorescence Staining and Histological Analysis of M(I/R)

24 Hours post-Ischemic/reperfusion, mice were sacrificed and hearts were perfused with cold PBS, fixed in 4% PFA for 24 hours and then embedded in the OCT compound (Sakura Finetek, Torrence Calif.). 10 µm thick cryosections were cut, stained with primary antibodies against Ly6G (Cat #108401, BioLegend, San Diego, Calif.) and biotin conjugated Isolectin GS-IB4 (Cat #I21414, Invitrogen). Cy3-conjugated streptavidin (Invitrogen) and fluorescein isothiocyanate (FITC)-conjugated anti-rat antibody were used as secondary reagents. Images were visualized by Confocal microscopy using an Olympus Fluoview FV10i.

Echocardiographic Studies

Cardiac dimensions and function were analyzed by transthoracic echocardiography using a Vevo 770 Imaging System (VisualSonics). Mice were lightly anesthetized with inhaled isoflurane (0.2% in $O_2$). Left ventricle M-mode was used, and all measurements were obtained from 3 to 6 consecutive cardiac cycles, and the average values were used for analysis. Left ventricle end-diastolic (LVDd) and end-systolic (LVDs) dimensions were measured from the M-mode traces, and fractional shortening (FS) was calculated as follows: [(LVDd" LVDs)/LVDd]. Diastolic measurements were taken at the point of maximum cavity dimension, and systolic measurements were made at the point of minimum cavity dimension, using the leading-edge method of the American Society of Echocardiography (Zhang, Y. et al., JCI Insight, 1, doi:10.1172/jci.insight.85484 (2016)).

Transient Middle Cerebral Artery Occlusion (tMCAO) and Treatments

Transient focal cerebral ischemia was induced in mice by middle cerebral artery occlusion (tMCAO) as was previously described (Kim, G. S. et al., Nature Communications, 6, 7893 (2015)). 33 mice (male, 24-28 g, C57BL6) were used in this study. The criterion for exclusion was development of subarachnoid hemorrhage. No animals were excluded from this study. Surgeries, as well as all behavioral and histological assessments were performed by an investigator blinded to the drug treatment. Mice were anesthetized with 3% isoflurane vaporized in $O_2$ for induction and 1.5% isoflurane for maintenance. Temperature was maintained at 36.5±0.5° C., controlled by a thermostatic blanket (CMA 450 Temp Controller for mice, Harvard Apparatus, Holliston, Mass.) throughout the procedure. The left common carotid artery was exposed and the occipital artery branches of the external carotid artery (ECA) were isolated and coagulated. The ECA was dissected distally and coagulated along with the terminal lingual and maxillary artery branches. The internal carotid artery (ICA) was isolated and the extracranial branch of the ICA was then dissected. A rubber silicone-coated monofilament suture (Filament size 6-0, diameter 0.09-0.11 mm, length 20 mm; diameter with coating 0.23±0.02 mm; coating length 5 mm, Doccol Corp., Sharon, Mass.) was introduced into the ECA lumen through an incision and then gently advanced approximately 9 to 9.5 mm in the ICA lumen to block MCA blood flow. For reperfusion, the suture was withdrawn 60 min after MCAO. 2-D laser speckle flowmetry (PeriCam PSI HR, Perimed, Jarfalla, Sweden) was used to confirm MCA occlusion and reperfusion. Right after removal of the suture, animals randomly received an intraperitoneal injection of PBS, apoM-$F_c$ or ApoM-TM-$F_c$.

Physiological parameters (arterial $O_2$ saturation, heart rate, pulse distention and respiratory rate) were recorded before, during and after tMCAO using the Mouse Ox Plus (Starr Life Sciences Corp., Oakmon, Pa.). After the surgery, all animals were maintained in a small animal heated recovery chamber (IMS Vetcare Chamber Recovery Unit, Harvard Apparatus, Holliston, Mass.). After recovery, animals were returned to their cages with free access to food and water. The mortality rate was 1/11 in PBS-treated mice, 0/11 in apoM WT and 1/11 in apoM-TM-treated mice.

Neurobehavioral Testing

Neurological function was evaluated at 23 h after reperfusion. Neurological deficit was graded on a score of 0 to 4 as previously described (Menzies, S. A. et al., *Neurosurgery*, 31, 100-106; discussion 106-107 (1992); Belayev, L. et al., *Stroke*, 27, 1616-1622; discussion 1623 (1996); Mokudai, T. et al., *Stroke*, 31, 1679-1685 (2000)): 0, no observable deficit; 1, forelimb flexion; 2, forelimb flexion and decreased resistance to lateral push; 3, forelimb flexion, decreased resistance to lateral push, and unilateral circling; and 4, forelimb flexion and being unable or difficult to ambulate.

TTC Staining and Determination of Infarct and Edema Ratios and Infarct Volumes 23 h after reperfusion, mice were anesthetized and decapitated. The brain was quickly removed from cranium, placed in −20° C. freezer for 20 min, and then cut into 1.5 mm coronal slices using a rodent brain matrix. Sections were stained with 2% 2,3,5-triphenyltetrazolium chloride (TTC) (Sigma Co., St. Louis, Mo.) at 37° C. for 10 min and scanned. Infarct area on each slice was determined by using Image analysis software (Image J, the National Institutes of Health, Bethesda, Md.) to obtain the infarct ratios, edema ratios and infarct volumes per brain (in millimeters$^3$). Infarct areas were calculated by using the following equation to correct for edema formation in the ischemic hemisphere (Swanson, R. A. et al., *J. of Cerebral Blood Flow and Metabolism*, 10, 290-293 (1990)): I=X−Y, where X is the area of the contralateral (non-ischemic) hemisphere and Y is the area of the intact regions of the ipsilateral (ischemic) hemisphere. Infarct ratios were obtained after normalization by the contralateral hemisphere. Edema ratios were calculated with the following formula: E=(Z−X)/X, where Z is the area of the ipsilateral hemisphere.

Statistical Analyses, Randomization and Blinding for Brain Studies

All values reported are mean±S.E.M. P values were calculated with GraphPad Prism software, using one-way non-parametric ANOVA (Kruskal Wallis) followed by Dunn's test. The criterion for statistical significance was set at P<0.05. All animal experiments used randomization to treatment groups and blinded assessment (Lapchak, P. A. et al., *J. of Neurology & Neurophysiology*, 4 (2013)).

Other Statistical Analysis

All statistical analyses were performed with Prism, version 4.03 (GraphPad Software, Inc., La Jolla, Calif., USA). Groups of 2 were compared by using two-tailed Student's t-test. Where appropriate, Welch's correction for unequal variances was applied. Analysis of Variance (ANOVA; 1-way or 2-way) was performed as indicated with either Tukey's post hoc test or Bonferroni's test for multiple comparisons. P % 0.05 indicated statistical significance.

Example 2: Development of Recombinant Soluble ApoM to Activate SW Receptors

Figures 1A, 1B, 1C:
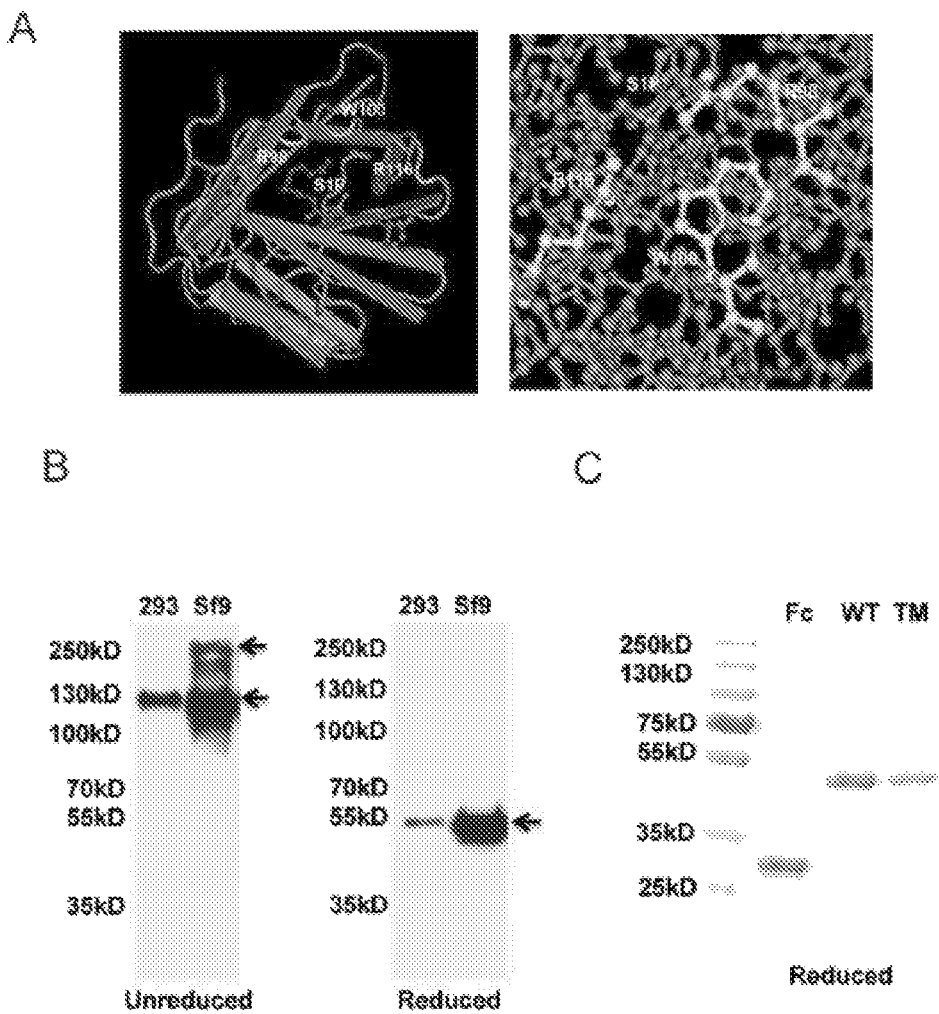
FIGS. 1A-1E. Production, purification and characterization of S1P binding by ApoM-$F_c$ and ApoM-$F_c$-TM fusion proteins. (A) (Left panel) Co-crystal structure of S1P bound to ApoM. Three residues, R98, W100 and R116 that contact the head group region of S1P are labeled. (Right panel) Space filling model of the head group region of S1P in the ApoM molecule. (B) ApoM-$F_c$ and ApoM-$F_c$-TM fusion proteins were expressed and purified from the conditioned media of HEK293 or Sf9 cells as described. Purified material was separated by non-reducing or reducing 10% SDS-PAGE and detected by anti-ApoM immunoblot. (C) Sf9-derived purified proteins (5 μg) were analyzed by reducing 10% SDS-PAGE and stained with Coomasie Blue. (D) Purified IgG1-Fc (Fc), ApoM-Fc, or ApoM-Fc-TM were analyzed for S1P binding by fluorescence spectrofluorimetry as described (N=4, expressed as Mean (+S.D.)). Data were analyzed Student's t-test and by 2-way ANOVA followed by Bonferroni's post-test comparing ApoM-$F_c$ or ApoM-$F_c$-TM to Fc alone (ApoM-$F_c$ (****, P<0.001) ApoM-$F_c$-TM (n.s.; not significant)). (E) Purified ApoM-$F_c$ and ApoM-$F_c$-TM (5 μM) were incubated or not with S1P as described for 24-48 h, purified by gel filtration chromatography and analyzed for sphingolipids by electrospray ionizing-tandem mass spectrometry (ESI-MS/MS). The resulting data are expressed as mean (+S.D.); N=4.

Free ApoM that is not associated with HDL has an extremely short half-life (Faber, K. et al., *Molecular Endocrinology*, 20, 212-218 (2006)). Hence, the inventors developed a strategy to stabilize ApoM in plasma by fusing it with the constant domain ($F_c$) of immunoglobulins. The ApoM-$F_c$ fusion protein was expressed in both HEK293 and insect Sf9 cells. Robust expression and efficient secretion of ApoM-$F_c$ into the conditioned medium was observed. An S1P binding mutant (R98A, W100A, and R116A), hereinafter referred to the ApoM-Fc-TM, containing mutations in three amino acid residues that contact the head region of the S1P molecule was also prepared (FIG. 1A). The purified proteins migrated as oligomers in non-reducing gels but was quantitatively reduced to a 50-55 kD monomer (FIG. 1B). Two-step purification procedure, consisting of Concanavalin A-affinity chromatography followed by gel filtration chromatography achieved highly purified ApoM-$F_c$ fusion protein at a yield of 7.8+2.7 μg/ml conditioned medium. ApoM-$F_c$-TM mutant was expressed and purified in a similar manner as the ApoM-$F_c$ fusion protein with a yield of 6.4+1.4 μg/ml. Both ApoM-$F_c$, ApoM-$F_c$-TM proteins as well as the IgG1-$F_c$ domain, were purified to homogeneity (FIG. 1C).

Figures 1D, 1E:
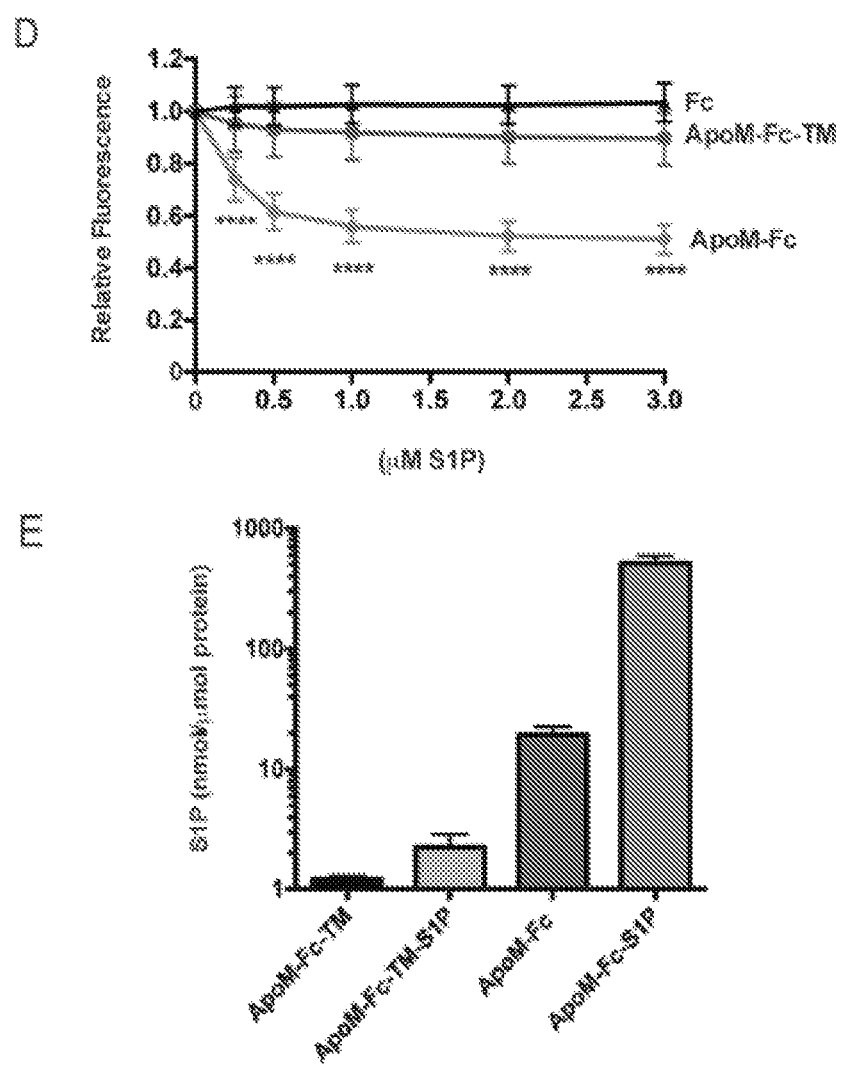

The ApoM-$F_c$ bound to S1P with an $EC_{50}$ of 0.22 μM (95% confidence interval: 0.168-0.336) whereas ApoM-$F_c$-TM and $F_c$ did not show significant binding activity (FIG. 1D). Further, Sf9 isolated ApoM-$F_c$ contained 1.94+0.31 mol % of S1P, presumably picked up from cells and/or cell culture medium. Incubation of ApoM-$F_c$ with S1P (1:8 mol/mol) for 24-48 hours at 4° C., followed by purification by gel filtration chromatography, yielded ApoM-$F_c$ containing 51.3+8.1 mol % of S1P (FIG. 1E). Purified ApoM-$F_c$-TM contained only 0.12+0.01 mol % of S1P; moreover S1P content was not increased stoichiometrically after incubation with exogenous S1P in vitro as above, consistent with the fact that the mutant does not bind to the lysophospholipid. S1P-enriched ApoM-$F_c$ is used for further signaling and biological experiments shown below.

Example 3: Sustained Activation of Endothelial Cell SW Receptors by S1P-Bound ApoM-$F_c$ Given that ApoM-$F_c$ binds to S1P, it was next determined whether ApoM-$F_c$ activates S1P receptors. ApoM-$F_c$ activated the β-arrestin-based S1P1 reporter (Kono, M. et al., *JCI*, 124, 2076-2086 (2014)) in a dose-dependent manner.

Figures 2A, 2B:
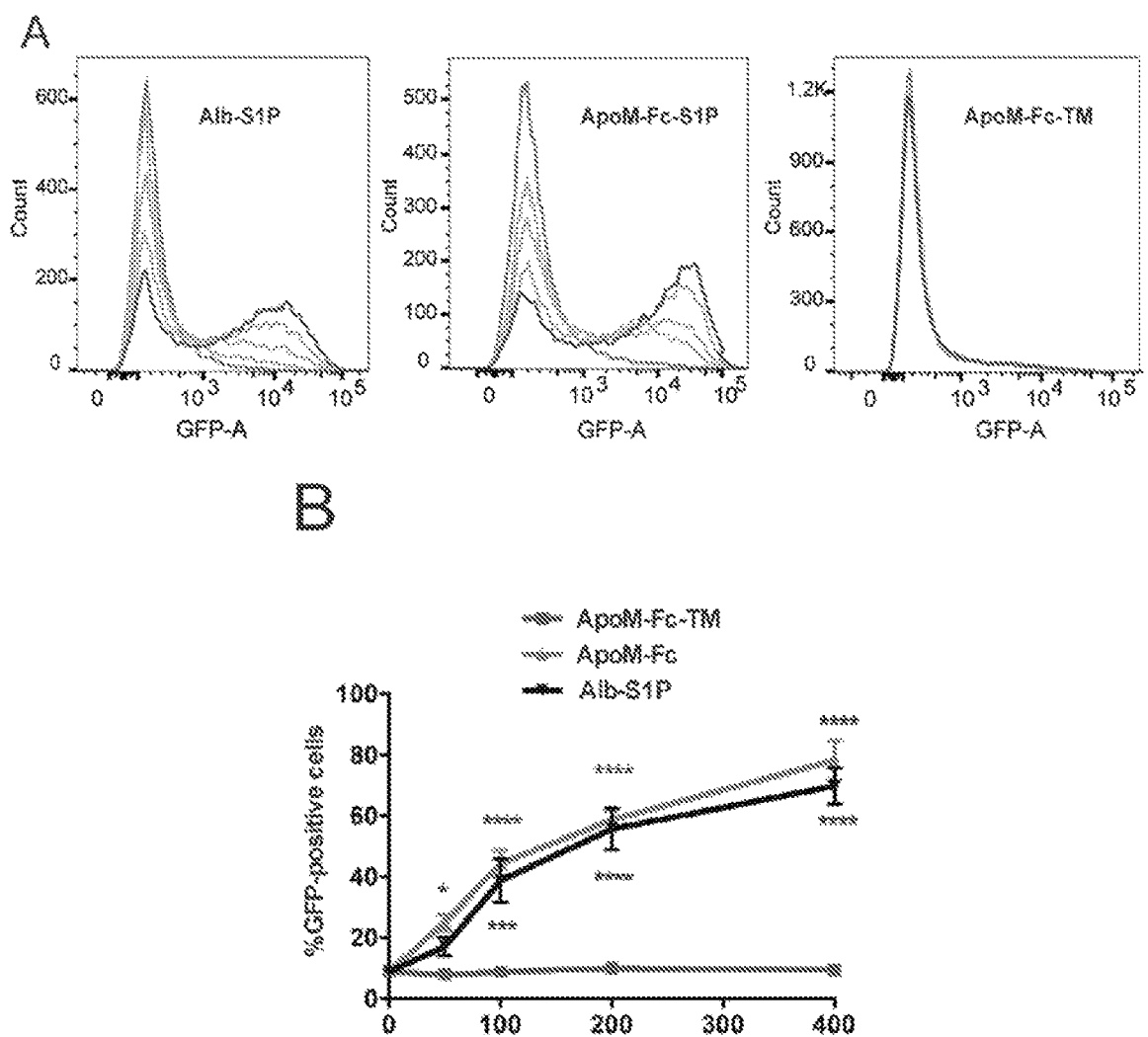
FIG. 2A-2D. ApoM-$F_c$ activates S1P receptors. (A) Increasing doses of albumin (Alb)-S1P, ApoM-$F_c$ or ApoM-$F_c$-TM were incubated with MEF cells isolated from $S1P_1$-GFP signaling mouse for 24 h and analyzed by flow cytometry. (B) Quantitative analysis of results from (A). N=3, expressed as Mean (+S.D.). Data were analyzed by two-way ANOVA followed by Bonferroni's post-test comparing ApoM-$F_c$ or BSA-S1P to ApoM-$F_c$-TM. (**, P<0.001; *, P<0.01) (C) CHO cells stably transduced with $S1P_1$ or $S1P_2$ or not were treated for 5 minutes using Albumin-S1P (100 nM S1P), ApoM-$F_c$-S1P (6-12 μg/ml; 60-120 nM S1P) or ApoM-$F_c$-TM (12 μg/ml) and analyzed for p44/42 ERK and Akt by immuno blot analysis. N=3; a representative blot is shown. (D) HUVEC (left panel) or CRISPR/Cas9 derived S1P1 KO HUVEC (middle and right panels) were treated with Albumin (Alb)-S1P (333 nM S1P), ApoM-Fc-S1P (20 μg/ml; 240 nM) or ApoM-$F_c$-TM (20 μg/ml) for indicated times and analyzed by immunoblot analysis for activation of p44/42 ERK, Akt and eNOS. CRISPR/Cas9 derived $S1P_1$ KO HUVEC were treated with ApoM-$F_c$-S1P (20 μg/ml; 240 nM S1P) with or without vehicle (DMSO), or $S1P_2$ inhibitor JTE-013 (10 μM), or $S1P_3$ inhibitor TY52156 (10
Figure 2C:
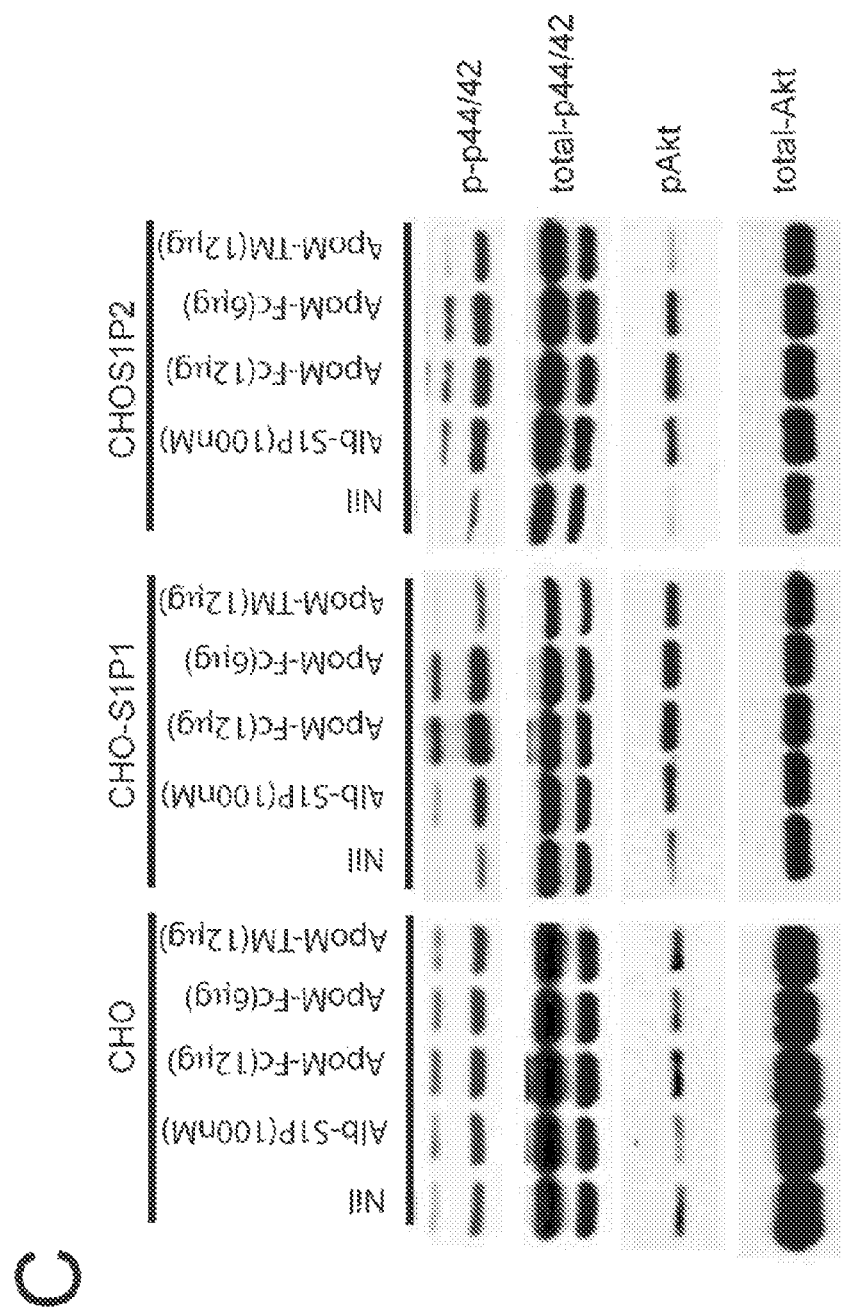
Figure 2D:
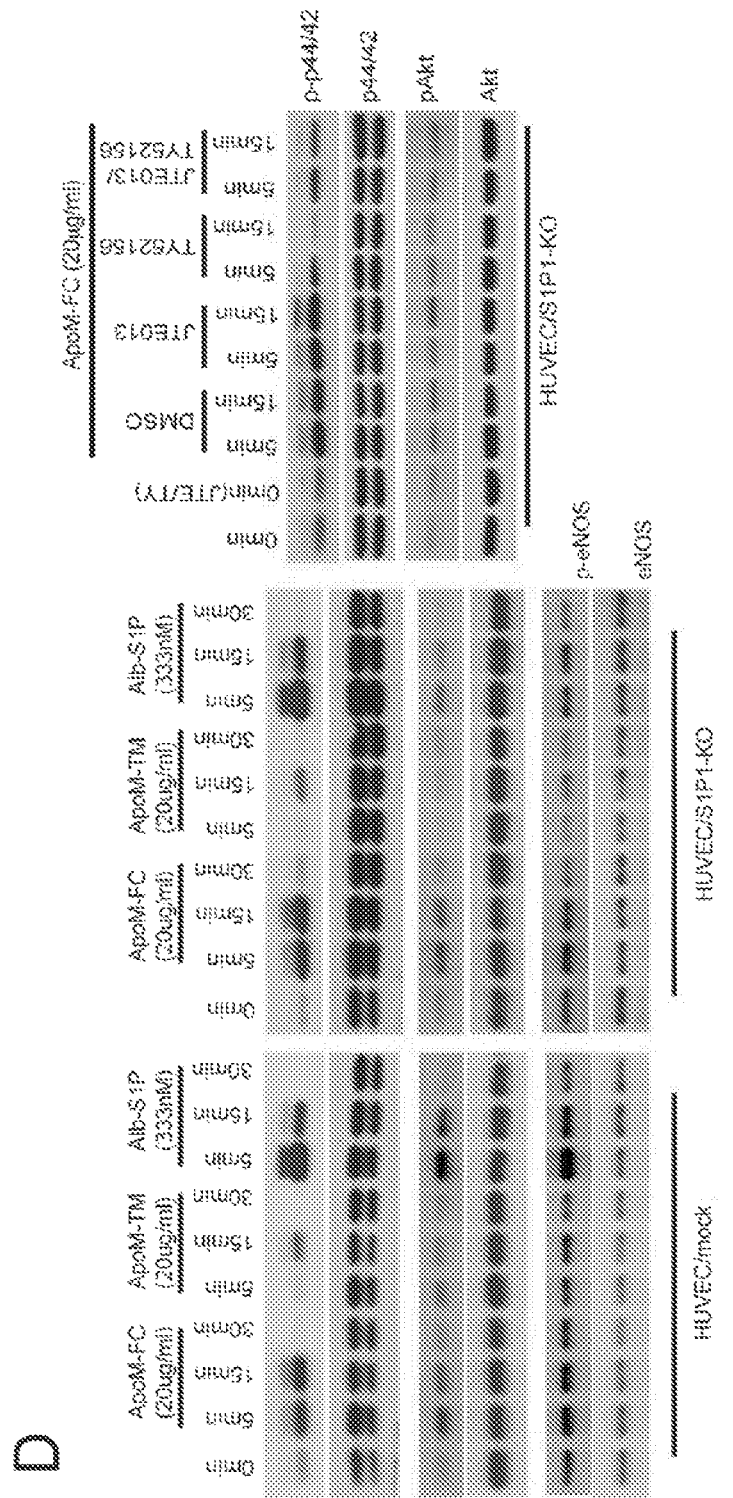

However, ApoM-F$_c$-TM was not active while albumin-S1P activated the reporter activity with a similar dose-response relationship (FIG. 2A, FIG. 2B). In CHO cells expressing S1P receptor subtypes 1 or 2, ApoM-F$_c$ but not ApoM-F$_c$-TM activated phosphorylation of the extracellular receptor-activated kinase phosphorylation (ppERK) and pAKT, which are known to be activated by S1P receptors via the G$_i$ pathway (FIG. 2C). In contrast, the effect of ApoM-F$_c$-TM was negligible. In human endothelial cells, ApoM-F$_c$ activated ppERK, pAKT and p-endothelial nitric oxide synthase (eNOS) through the S1P1 and S1P3 receptors (FIG. 2D). These data suggest that ApoM-F$_c$ is capable of activating S1P$_{1-3}$ receptors.

Activation of endothelial cell S1P$_1$ and S1P$_3$ receptors results in the assembly of adherens junctions and the enhancement of barrier function (McVerry, B. J. et al., *J. of Cellular Biochem.*, 92, 1075-1085 (2004)), which can be measured by increased trans-endothelial electrical resistance (TEER). HDL-bound S1P is more potent in the promotion of vascular barrier compared to albumin-S1P in vitro and in vivo (Christensen, P. M. et al., *FASEB J.* (2016); Christoffersen, C. et al., *PNAS*, 108, 9613-9618 (2011)). When a monolayer of HUVEC was treated with ApoM-F$_c$, a sustained increase in TEER was observed. In contrast, ApoM-F$_c$-TM did not increase TEER. While albumin-bound S1P also enhanced TEER, the increase was transient. The ability of ApoM-F$_c$ to increase TEER is dependent on S1P$_1$ signaling, since it was greatly attenuated in HUVEC that were designed to lack S1P$_1$ by CRISPR/Cas9-mediated gene disruption (FIG. 3A, FIG. 3B). In addition, even though ApoM-F$_c$ induced internalization of S1P$_1$ receptor, the extent of internalization was lower than that induced by FTY720-P or albumin-bound S1P (FIG. 3C). These data suggest that ApoM-F$_c$ induces sustained enhancement of endothelial cell barrier function by activating S1P receptors.

Example 4: In Vivo Stability of ApoM-F$_c$ Bound S1P

In vivo stability of the ApoM-F$_c$ and ApoM-F$_c$-TM was determined by measurement of plasma levels following intra-peritoneal injection. ApoM-F$_c$ and ApoM-F$_c$-TM showed plasma half lives of 93.5 hours and 86.5 hours, respectively, suggesting that they are highly stable in vivo (FIG. 4A). When 100 µg of ApoM-F$_c$ was injected, plasma S1P and dihydro-S1P levels increased 76.3+13.7%; 52.9+12.9% and 29.9+10.1%; 38.9+4.1% 24 h thereafter in Apom$^{-/-}$ and WT mice, respectively. Plasma levels of sphingosine, dihydrosphingosine and ceramides as well as cholesterol were unaffected (FIG. 4B, FIG. 4C). Injected ApoM-F$_c$ was not associated with HDL fraction and is found in the lipoprotein-free fraction. These data suggest that ApoM-F$_c$ stabilizes bound S1P as a soluble protein in vivo, presumably due to protection from phosphatase-mediated degradation. It was previously that albumin-bound S1P is rapidly degraded in vivo with an estimated half-life of 15 min (Venkataraman, K. et al., *Circulation Research*, 102, 669-676 (2008)). This property explains, at least in part, the sustained biological effects of ApoM-F$_c$.

Figures 4D, 4E, 4F, 4G:
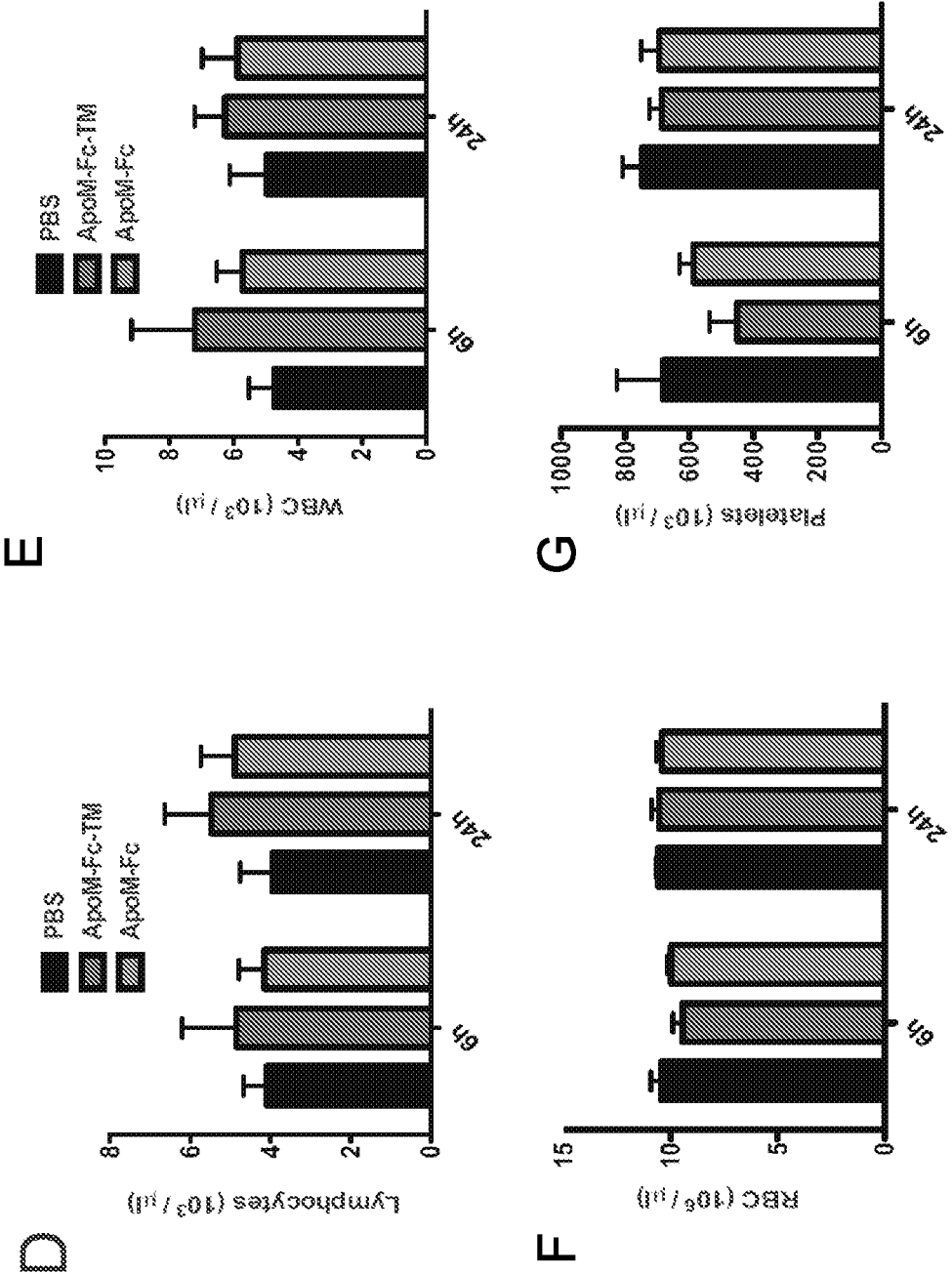

Example 5: In Vivo Effects of ApoM-F$_c$ Bound SW on Hematopoietic Cell Trafficking ApoM-F$_c$ administration and resultant elevation of plasma S1P could potentially activate lymphocyte S1P$_1$ receptor to modulate lymphocyte egress and platelet formation (Cyster, J. G. & Schwab, S. R., *Annual Review of immunology*, 30, 69-94 (2012); Zhang, L. et al., *The Journal of Experimental Medicine*, 209, 2165-2181 (2012)). Therefore, circulating blood cells were quantified after ApoM-F$_c$ administration. As shown in FIG. 4D, circulating levels of white blood cells, lymphocytes, platelets and red blood cells were not altered by ApoM-F$_c$ or ApoM-F$_c$-TM administration, suggesting that immune and hematopoietic S1P receptors are not activated by ApoM-F$_c$ administration. This is in sharp contrast to small molecule S1P$_1$ modulators, which induce lymphopenia due to their functional antagonism in the secondary lymphoid organs, thymus and the spleen (Cyster, J. G. & Schwab, S. R., *Annual Review of immunology*, 30, 69-94 (2012)). It is likely that ApoM-F$_c$ does not access hematopoietic S1P$_1$ receptor in lymphoid and/or hematopoietic tissues.

Figures 5A, 5B, 5C, 5D, 5E:
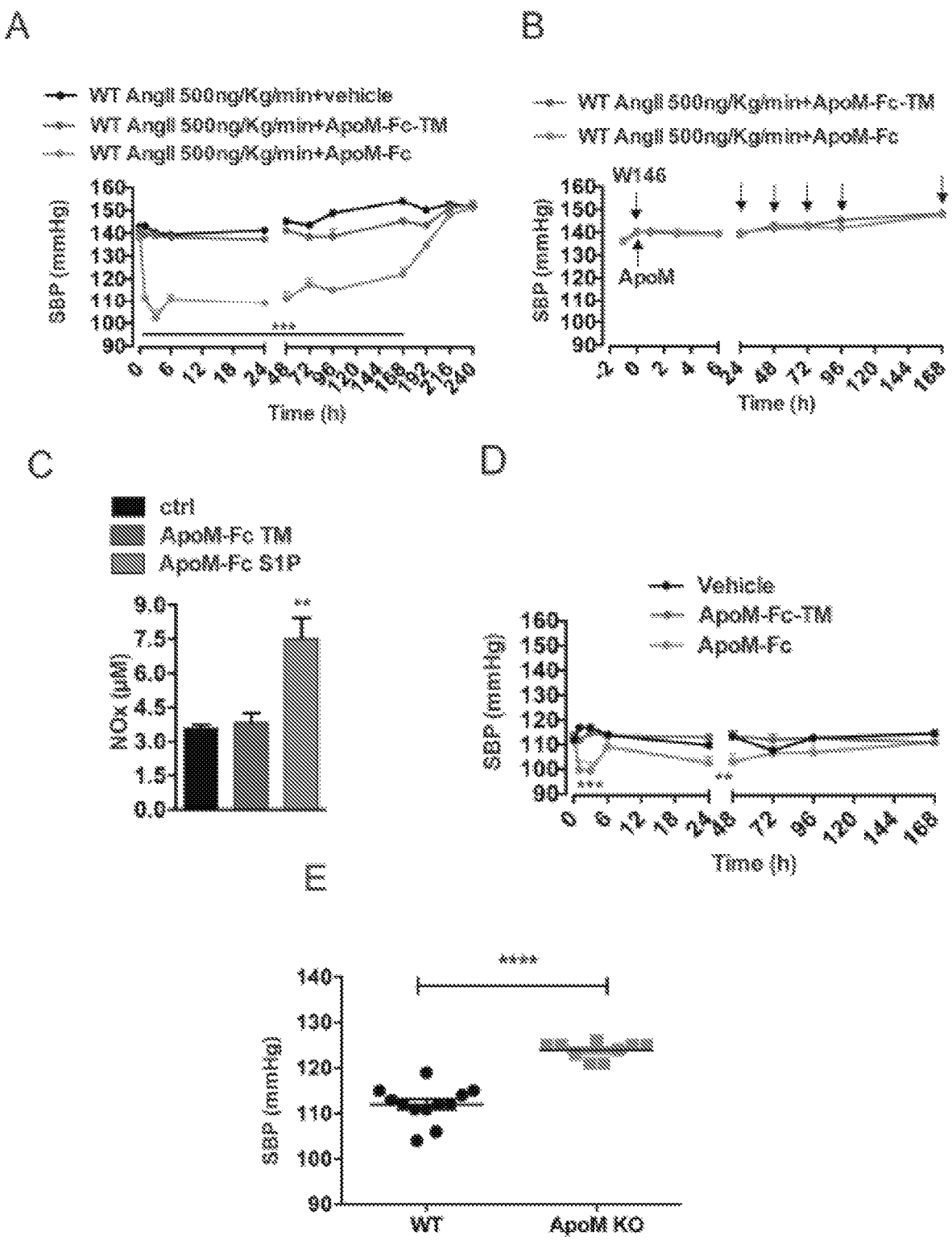

Example 6: Sustained Blood Pressure Reduction in Hypertensive Mice After ApoM-F$_c$ Administration Endothelial dysfunction contributes to hypertensive pathophysiology. Indeed, plasma S1P levels modulate vascular tone by stimulating eNOS activity (Nofer, J. R. et al., *JCI*, 113, 569-581 (2004); Cantalupo, A. et al., *Nature Medicine*, 21, 1028-1037 (2015)) while endothelial S1P$_1$ stimulates eNOS activity via the protein kinase Akt (Christoffersen, C. et al., *PNAS*, 108, 9613-9618 (2011); Igarashi, J. et al., *Biochimica et Biophysica Acta*, 1781, 489-495 (2008)). It was therefore investigated if ApoM-F$_c$ administration modulated blood pressure in hypertensive mice implanted with Angiotensin-II osmotic minipump. In C56/B16 mice, ApoM-F$_c$ but not ApoM-F$_c$-TM administration potently reduced blood pressure 40 mmHg at 2 hours post treatment (FIG. 5A). The effect of ApoM-F$_c$ was sustained and therapeutic efficacy was maintained for 192 hours after a single dose. This profound and sustained decrease in blood pressure was completely abolished by co-administration with W146 (10 mg/kg), a competitive antagonist for S1P$_1$ (FIG. 5B). In hypertensive mice, plasma nitrite levels were strongly induced by ApoM-F$_c$ but not by ApoM-F$_c$-TM (FIG. 5C). Resting blood pressure in normal mice was decreased transiently by ApoM-F$_c$ but the magnitude and duration was less potent and transient (FIG. 5D). Indeed, Apom$^{-/-}$ mice show significantly elevated resting blood pressure compared to the WT counterparts (FIG. 5E). These data suggest that ApoM-F$_c$ administration activates endothelial S1P1/eNOS/NO axis to achieve a sustained anti-hypertensive effect. In contrast to ApoM-F$_c$, administration of small molecules that target the S1P$_1$ receptor induces a mild elevation of blood pressure in rodents and humans, in part due to their functional antagonism of endothelial S1P1 (Cantalupo, A. et al., *Nature Medicine*, 21, 1028-1037 (2015); Camm, J. et al., *American Heart Journal*, 168, 632-644 (2014)).

Figure 6A:
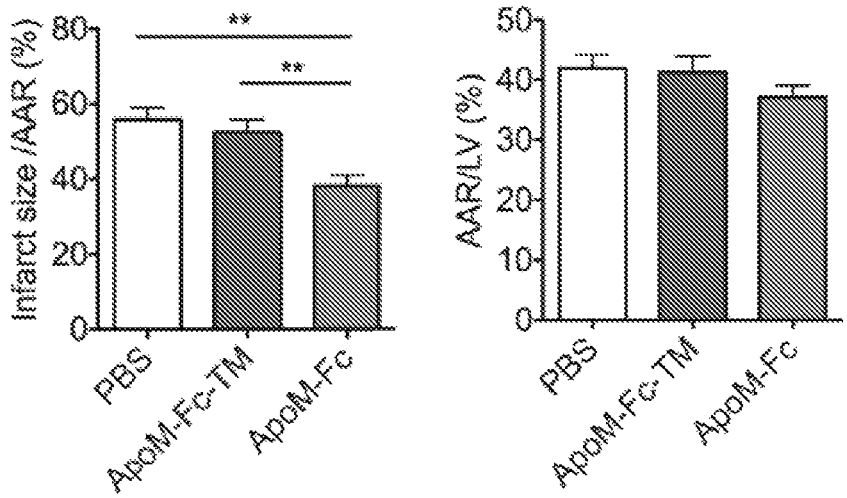
Figure 6B:
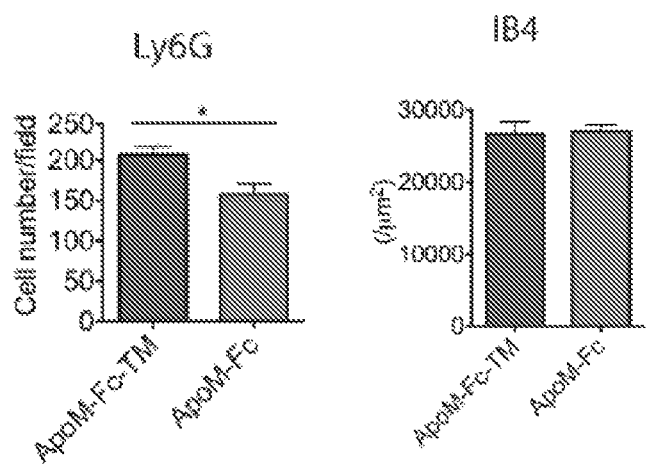
Figure 6C:
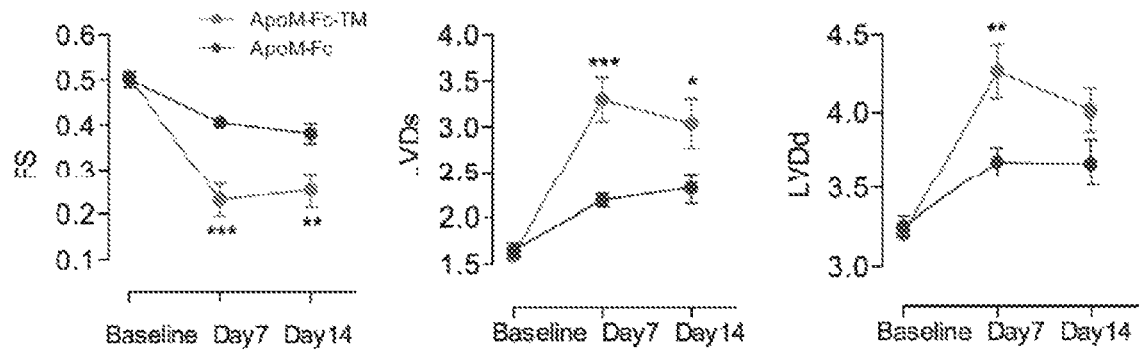

Example 7: Effect of ApoM-F$_c$-Bound S1P on Cardiac Function After Myocardial Infarction HDL and S1P are known to suppress ischemia/reperfusion (I/R) injury in rodent and porcine models of myocardial infarction (Morel, S. et al., *Cardiovascular Research*, 109, 385-396 (2016); Sattler, K. et al., *Journal of the American College of Cardiology*, 66, 1470-1485 (2015); Theilmeier, G. et al., *Circulation*, 114, 1403-1409 (2006); Santos-Gallego, C. G. et al., *Circulation*, 133, 954-966 (2016)) and in rodent models of stroke (Lapergue, B. et al., *Stroke*, 44, 699-707 (2013); Wei, Y. et al., *Annals of Neurology*, 69, 119-129 (2011)). In stroke patients undergoing reperfusion therapies, HDL cholesterol levels were associated with a favorable outcome at 3 months (Makihara, N. et al., Cerebrovascular Diseases, 33, 240-247 (2012)). In the heart, therapeutic administration of S1P1 agonists also suppress I/R injury (Levkau, B., Frontiers in Pharmacology, 6, 243 (2015)) even though a small molecule agonist (SEW2871) induced abnormal cardiac rhythm (Hofmann, U. et al., Cardiovascular Res., 83, 285-293 (2009); Tsukada, Y. T. et al., Journal of Cardiovascular Pharmacology, 50, 660-669 (2007)). The inventors therefore hypothesized that ApoM-$F_c$ administration would attenuate myocardial I/R injury due to its protective effect on the endothelium. ApoM-$F_c$ but not ApoM-$F_c$-TM administration reduced I/R injury at 24 h post-reperfusion (FIG. 6A). In addition, neutrophil accumulation into the infarcted site was greatly attenuated by ApoM-$F_c$ but vascular density was not altered at the infarcted site, suggesting that ApoM-$F_c$ maintained endothelial homeostasis after myocardial I/R injury (FIG. 6B). Echocardiographic analysis 1-2 weeks after I/R injury showed that significant preservation of myocardial function by ApoM-$F_c$ administration (FIG. 6C). These data suggest that therapeutic administration of ApoM-$F_c$ activates vascular S1P receptors to suppress myocardial I/R injury.

Figures 6D, 6E, 6F, 6G, 6H:
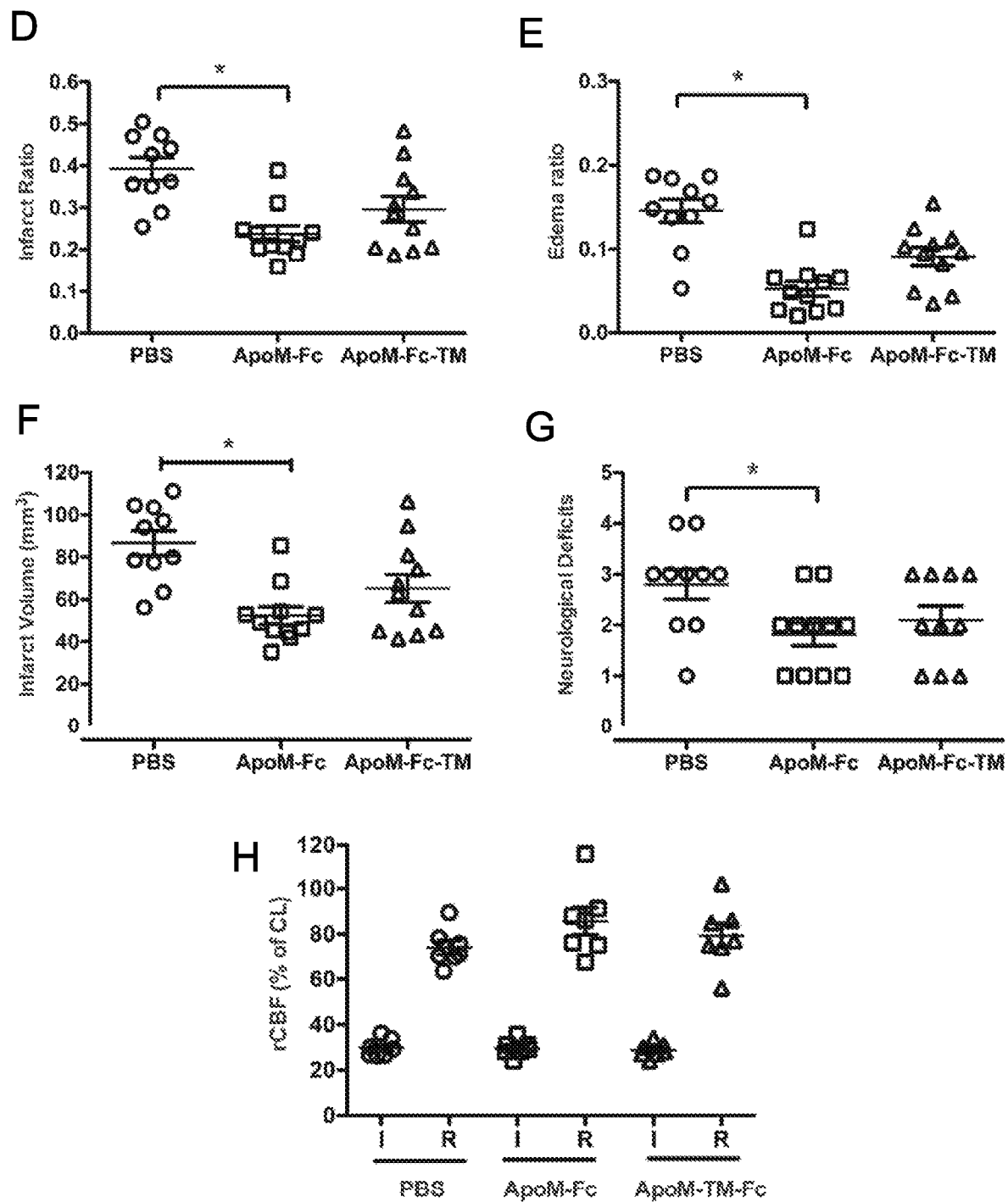

In order to investigate the therapeutic potential of ApoM-$F_c$ treatment in cerebral ischemia, a mouse model of transient focal cerebral ischemia, the middle cerebral artery occlusion (MCAO) model, was used. After 60 minutes of ischemia, mice were treated with PBS, ApoM-$F_c$ or ApoM-TM-$F_c$ (I.P. injection, 4 mg/kg) at the time of reperfusion. Twenty three hours after reperfusion, edema and infarct ratios as well as infarct volumes were calculated as previously described (Kim, G. S. et al., Nature Communications, 6, 7893 (2015)). As shown in FIGS. 6D-F, administration of ApoM-$F_c$ resulted in a significant decrease in both the infarct ratios (PBS-treated mice 0.393±0.026 vs ApoM-$F_c$-treated mice 0.238±0.019; 39% reduction) and the total edema ratios (PBS-treated mice 0.146±0.013 vs ApoM-$F_c$-treated mice 0.052±0.009, 64% reduction), which is the sum of cytotoxic and vasogenic edema. Infarct volumes (corrected for edema) were significantly lower in ApoM-$F_c$ treated mice (52.4±4.2 mm$^3$) compared to PBS-treated mice (86.8±5.8 mm$^3$). In contrast, treatment with ApoM-TM-$F_c$ trended towards a protective effect, which did not achieve statistical significance. It was also found that the neurological scores were significantly improved in ApoM-$F_c$ treated mice compared to PBS-treated mice but not in mice treated with ApoM-TM-$F_c$ (FIG. 6G). Cerebral blood flow the territory of the MCA monitored during the surgeries by Laser speckle flowmetry, was similarly reduced in all three groups of mice during occlusion and similarly restored after reperfusion (FIG. 6H). These data indicate that in experimental stroke, ApoM-$F_c$ treatment after reperfusion potently decreases total cerebral edema and infarct size resulting in improved stroke outcomes. The physiological parameters (arterial oxygen saturation, heart rate, pulse distention and respiratory rate), measured before, during ischemia and after reperfusion (Kim, G. S. et al., Nature Communications, 6, 7893 (2015)), were not significantly changed in mice treated with PBS, ApoM-$F_c$ or ApoM-TM-$F_c$.

The results disclosed herein suggest that ApoM-$F_c$ recombinant protein binds to S1P and activates endothelial S1P receptors. The ApoM-$F_c$ recombinant protein is stable in vivo, therefore, allows sustained activation of S1P receptors in the vasculature. Interestingly, the ApoM-$F_c$ treatment does not induce lymphopenia, suggesting that it does not access lymphocyte S1P receptors in secondary lymphoid organs. This suggests that ApoM-$F_c$ administration selectively targets endothelial S1P receptors and affords a novel strategy to therapeutically modulate S1P-dependent vascular pathology in vivo. Indeed, administration of ApoM-$F_c$ recombinant protein achieved sustained reduction in blood pressure in hypertensive mice. This effect is dependent on S1P1 activation and involves NO synthesis. Therapeutic targeting of this pathway may be useful in therapy-resistant hypertensive syndromes. Moreover, evidence is presented herein that ApoM-$F_c$ recombinant protein suppresses myocardial I/R injury in a mouse model. Previous work has shown that HDL infusion or S1P$_1$ agonists protect the myocardium from MI/R injury (Morel, S. et al., Cardiovascular Research, 109, 385-396 (2016); Sattler, K. et al., Journal of the American College of Cardiology, 66, 1470-1485, (2015); Theilmeier, G. et al., Circulation, 114, 1403-1409 (2006); Santos-Gallego, C. G. et al., Circulation, 133, 954-966 (2016)). In addition, in mouse models of stroke, HDL infusion and S1P$_1$ receptor activators were shown to reduce neuronal I/R injury in animal models and in human clinical trials (Makihara, N. et al., Cerebrovascular Diseases, 33, 240-247 (2012); Keene, D. et al., BMJ, 349, g4379 (2014); Lapergue, B. et al., Stroke, 44, 699-707 (2013); Wei, Y. et al., Annals of Neurology, 69, 119-129 (2011); Kim, G. S. et al., Nature Communications, 6, 7893 (2015); Fu, Y. et al., PNAS, 111, 18315-18320 (2014); Zhu, Z. et al., Circulation, 132, 1104-1112 (2015)). The ability to selectively activate vascular S1P receptors with ApoM-$F_c$ recombinant protein provides significant advantages to small molecules that target this pathway. Indeed, small molecule S1P$_1$ inhibitors are not selective for the vasculature and short-term agonism evolves into chronic functional antagonism that influences many organ systems (Hla, T., Neurology, 76, S3-8 (2011)). Thus ApoM-$F_c$ administration is proposed herein as a novel therapy for diseases in which endothelial function is compromised.

What is claimed is:

1. A fusion protein comprising an Apolipoprotein M (ApoM) polypeptide fused to a fragment crystallizable (Fc) region of an antibody, wherein the ApoM polypeptide comprises amino acids 21-188 of SEQ ID NO: 9 and does not comprise amino acids 1-20 of SEQ ID NO: 9.

2. The fusion protein of claim 1, wherein the fusion protein further comprises an IL-2 signal peptide at the amino-terminus.

3. The fusion protein of claim 1, wherein the Fc region is fused to the amino terminus of the ApoM polypeptide.

4. The fusion protein of claim 2, wherein the Fc region is fused to the carboxyl terminus of the ApoM polypeptide.

5. The fusion protein of claim 1, wherein the Fc region is an Fc region selected from the group consisting of an IgG antibody, an IgM antibody, an IgA antibody, an IgE antibody, and an IgD antibody.

6. The fusion protein of claim 5, wherein the Fc region is an IgG1-Fc.

7. A composition comprising the fusion protein of claim 1 in complex with phospholipids or lysophospholipids.

8. The composition of claim 7, wherein the phospholipids comprise phosphocholine.

9. The composition of claim 7, wherein the phospholipids comprise sphingosine 1-phosphate (S1P).

10. The composition of claim 7, wherein the composition is formed by mixing the fusion protein with the phospholipids or the lysophospholipids, incubating the mixture to allow the complex to form, and purifying the complex.

11. The composition of claim 10, wherein the phospholipids comprise phosphocholine.

12. The composition of claim 10, wherein the phospholipids comprise sphingosine 1-phosphate (S1P).

13. A method of treating a condition in a subject, comprising administering a composition according to claim 9 to the subject, wherein said condition is selected from the group consisting of hypertension, ischemia of the heart, ischemia of the brain, accelerated atherosclerosis, non-cardiac reperfusion injury and peripheral vascular disease.

14. The method of claim 13, wherein said hypertension comprises conditions selected from the group consisting of primary resistant hypertension, secondary resistant hypertension, neurogenic hypertension, gestational hypertension (pre-eclempsia), diabetic pre-eclempsia, and hypertension of chronic kidney disease.

15. The method of claim 13, wherein said ischemia of the heart comprises diseases selected from the group consisting of cardiac reperfusion injury, myocardial infarction, acute coronary syndrome and angina.

16. The method of claim 13, wherein said non-cardiac reperfusion injury comprises an injury as a result of an ischemia selected from the group consisting of liver ischemia, kidney ischemia, intestinal ischemia, and muscle ischemia.

17. A method of reducing a side effect of Fingolimod in a patient being treated with Fingolimod comprising administering the ApoM-Fc fusion protein of claim 1 to the patient.

* * * * *

UNITED STATES PATENT AND TRADEMARK OFFICE
CERTIFICATE OF CORRECTION

PATENT NO. : 10,870,689 B2
APPLICATION NO. : 16/326089
DATED : December 22, 2020
INVENTOR(S) : Timothy T. Hla et al.

It is certified that error appears in the above-identified patent and that said Letters Patent is hereby corrected as shown below:

On the Title Page

At item (73) Assignee, please replace:
"The Children's Medical Center Corporation, Boston, MA (US)"

With:
--Children's Medical Center Corporation, Boston, MA (US)--

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Oligonucleotide

<400> SEQUENCE: 1
tatccatggg gatctaccag tgccctgagc acagt                                    35

<210> SEQ ID NO 2
<211> LENGTH: 35
<212> TYPE: DNA
<213> ORGANISM: Artificial Sequence
<220> FEATURE:
<223> OTHER INFORMATION: Oligonucleotide

<400> SEQUENCE: 2
tatggatcct ccgttattgg acagctcaca ggcct                              35

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
cgccctgcca tggcgactga gctc                                          24

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
aatcatgctg aatgcgacag gcc                                           23

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide

<400> SEQUENCE: 5
tatggatcca tgtacaggat gcaactcctg tctt                               34

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide

<400> SEQUENCE: 6
tatttatcat gtctggccag ctagcgacac tggg                               34

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide

<400> SEQUENCE: 7
caccgcggga cgctggtggg cccca                                         25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide

<400> SEQUENCE: 8
aaactggggc ccaccagcgt cccgc                                                                          25

<210> SEQ ID NO 9
<211> LENGTH: 188
<212> TYPE: PRT
<213> ORGANISM: Homo sapiens

<400> SEQUENCE: 9

Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
            20                  25                  30

Gly Val Asp Gly Lys Glu Phe Pro Glu Val His Leu Gly Gln Trp Tyr
        35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185

<210> SEQ ID NO 10
<211> LENGTH: 190
<212> TYPE: PRT
<213> ORGANISM: Mus musculus

<400> SEQUENCE: 10

Met Phe His Gln Val Trp Ala Ala Leu Leu Ser Leu Tyr Gly Leu Leu
1               5                   10                  15

Phe Asn Ser Met Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Ser Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser

```
                115                 120                 125
Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160

Glu Glu Phe Gln Ser Leu Thr Ser Cys Leu Asp Phe Lys Ala Phe Leu
                165                 170                 175

Val Thr Pro Arg Asn Gln Glu Ala Cys Pro Leu Ser Ser Lys
                180                 185                 190
```